(12) United States Patent
Pullman et al.

(10) Patent No.: US 6,492,174 B1
(45) Date of Patent: Dec. 10, 2002

(54) METHODS OF INITIATING EMBRYOGENIC CULTURES IN PLANTS

(75) Inventors: Gerald S. Pullman, Alpharetta; Gary Peter, Atlanta, both of GA (US)

(73) Assignee: Institute of Paper Science & Technology, Atlanta, GA (US)

( * ) Notice: Subject to any disclaimer, the term of this patent is extended or adjusted under 35 U.S.C. 154(b) by 7 days.

(21) Appl. No.: 09/685,338

(22) Filed: Oct. 11, 2000

Related U.S. Application Data
(60) Provisional application No. 60/212,651, filed on Jun. 19, 2000.

(51) Int. Cl.$^7$ .............................. C12N 5/00; C12N 5/02
(52) U.S. Cl. ........................ 435/422; 435/420; 435/410
(58) Field of Search ................................ 435/422, 410, 435/420

(56) References Cited

U.S. PATENT DOCUMENTS

| | | |
|---|---|---|
| 4,957,866 A | 9/1990 | Gupta et al. |
| 5,034,326 A | 7/1991 | Pullman et al. |
| 5,036,007 A | 7/1991 | Gupta et al. |
| 5,236,841 A | 8/1993 | Gupta et al. |
| 5,294,549 A | 3/1994 | Pullman et al. |
| 5,413,930 A | 5/1995 | Becwar et al. |
| 5,491,090 A | 2/1996 | Handley, III et al. |
| 5,506,136 A | 4/1996 | Becwar et al. |
| 5,565,355 A | 10/1996 | Smith |
| 5,677,185 A | 10/1997 | Handley, III |
| 5,856,191 A | 1/1999 | Handley, III |
| 5,965,488 A | 10/1999 | Sakai et al. |

OTHER PUBLICATIONS

Wang et al; Effects of brassinolide on somatic embryogenesis of Gossypium hirsutum, Plant Physiology Communications, 1992, 28 (1):pp. 15–18.*

Yang et al; A study of factors affecting anther culture of cauliflower (*Brassica oleracea var. botryis*), Plant Cell, Tissue and Organ Tissue, 1992, 28 (3):pp. 289–296.*

Anno et al., "Matric Potential and Overburden Potential in Gels for Plant Tissue Culture," *Environment Control In Biology*, vol. 37, No. 2, pp. 129–135, Jun. 1999.

Barthou et al., "Effect of atmospheric pressure on sunflower (*Helianthus annuus*) protoplast division," *Plant Cell Reports*, pp. 310–314, 1997.

Becwar et al., Initiation of embryogenic cultures and somatic embryo evelopment in loblolly pine (*Pinus taeda*), *Canadian Journal of Forest Research*, vol. 20, No. 6, pp. 810–817, Jun. 1990.

Becwar et al., "Development and Characterization of In Vitro Embryogenic Systems In Conifers," *Somatic Cell Genetics of Woody Plants*, pp. 1–18, Aug. 10–13, 1988.

Brosa, "Biological Effects of Brassinosteroids," *Critical Reviews in Biochemistry and Molecular Biology*, vol. 34, No. 5, pp. 339–358, 1999.

Chalupa, Somatic Embryogenesis and Plant Regeneration in Norway Spruce (*Picea abies*/L./Karst.), *Acta Universitatis Carolinae Biologica*, 41, pp. 13–22, 1997.

Etienne et al., "Water status of callus from *Hevea brasiliensis* during induction of somatic embryogenesis," *Physiologia Plantarum*, vol. 82, pp. 213–218, Jun. 1991.

Finer et al., "Initiation of embryogenic callus and suspension cultures of eastern white pine (*Pinus strobus* L.)," *Plant Cell Reports*, vol. 8, pp. 203–206, 1989.

Ghashgaie et al., "Effects of agar concentration on water status and growth of rose plants cultured in vitro," *Physiologia Plantarum*, vol. 82, pp. 73–78, May 1991.

Gupta et al., "Liquid Media and Automation Strategy for Large–scale Production of Conifer Somatic Embryos for Reforestation," *In Vitro Cellular & Developmental Biology*, vol. 35, No. 3, Part II, Mar. 1999, p. 22–A.

Harry et al., "Somatic Embryogenesis and Plant Regeneration From Mature Zygotic Embryos of Red Spruce," *Botanical Gazette*, vol. 152, No. 4, pp. 446–452, Dec. 1991.

Jain et al., "Somatic Embryogenesis in Slash Pine (*Pinus Elliottii*) From Immature Embryos Cultured In Vitro," *Plant Science*, vol. 65, pp. 233–241, 1989.

Johansson, "Effects of activated charcoal in anther cultures," *Physiologia Plantarum*, vol. 59, pp. 397–403, Nov. 1983.

Kim et al., "Identification of Two Brassinosteroids from the Cambial Region of Scots Pine (*Pinus silverstris*) By Gas Chromatography–Mass Spectrometry, after Detection Using a Dwarf Rice Lamina Inclination Bioassay," *Plant Physiol.*, vol. 94, pp. 1709–1713, Mar. 19, 1990.

Kong et al., "Effects of silver nitrate and polyethylene glycol on white spruce *Picea glauca*) somatic embryo development: enhancing cotyledonary embryo formation and endogenous ABA content," *Physiologia Plantarum*, vol. 93, pp. 298–304, 1995.

Kumar et al., "Ethylene and Carbon Dioxide Accumulation, and Growth of Cell Suspension Cultures of *Picea glauca* (White Spruce)," *J. Plant. Physiol.*, vol. 135, No. 5, pp. 592–596, Jan. 1989.

(List continued on next page.)

*Primary Examiner*—Bruce R. Campell
*Assistant Examiner*—June Hwu
(74) *Attorney, Agent, or Firm*—Finnegan, Henderson, Farabow, Garrett & Dunner, LLP

(57) ABSTRACT

The present invention provides methods for initiating embryogenic cultures of plants. The methods include the use of novel media compositions and elevated atmospheric pressure treatments to improve the frequency of embryogenic culture initiation. The methods are well suited for initiating embryogenic cultures in recalcitrant conifer varieties. The method is also well suited for producing somatic embryos that can be further cultured to produce large numbers of plants. Further, the invention provides novel methods that may be used to enhance somatic embryogenesis in a broad range of species.

43 Claims, No Drawings

OTHER PUBLICATIONS

Kvaalen et al., "Effects of various partial pressures of oxygen and carbon dioxide on different stages for somatic embryogenesis in *Picea abies*," *Plant Cell Tissue and Organ Culture,* vol. 27, pp. 49–57, Oct. 1991.

Kvaalen et al., "Oxygen influences benzyladenine and 2,4–dichlorophenoxyacetic acid levels in cultured embryogenic tissue of Norway spruce," *Physiologia Plantarum,* vol. 88, pp. 571–576, Aug. 1993.

Li et al., "Induction of Somatic Embryogenesis in Loblolly Pine (*Pinus Taeda* L.)," *In Vitro Cellular & Developmental Biology,* vol. 32, No. 3, pp. 129–135, Jul.–Sep. 1996.

Majada et al., "in Vitro Culture In Liquid Media: A Requirement For Automatization," *Acta Horticulturae,* vol. 289, p. 239, 1991.

El Meskaoui et al., "Effects of sealed and vented gaseous microenvironments on the maturation of somatic embryos of black spruce with a special emphasis on ethylene," *Plant Cell, Tissue and Organ Culture,* vol. 56, pp. 201–209, 1999.

Michler et al., "Effects of embryo explant type and developmental maturity on Easter White Pine(*Pinus strobes*L.) embryogenic callus initiation," Abstracts of Papers Presented at the International Symposium on Applications of Biotechnology to Tree Culture, Protection and Utilization, Aug. 5–8, 1991.

Murashige et al., "A Revised Medium for Rapid Growth and Bio Assays with Tobacco Tissue Cultures," *Physiologia Plantarum,* vol. 15, pp. 473–497, 1962.

Owens et al., "Measurement and effects of gel matric potential and expressibility on production of morphogenic callus by cultured sugarbeet leaf discs," *Plant Cell, Tissue and Organ Culture,* vol. 26, pp. 127–133, 1991.

Rönsch et al., "Influence of (22S,23S)–homobrassinolide on rooting capacity and survival of adult Norway spruce cuttings," *Tree Physiology,* vol. 12, pp. 71–80, Jan. 1993.

Roth et al., "Brassinosteroids: Potent Inhibitors of Growth of Transformed Tobacco Callus Cultures," *Plant Science,* vol. 59, pp. 63–70, 1989.

Sasse et al., "Brassinosteroids and Transplantation Stress," *Abstract—Nineteenth Annual Meeting of Plant Growth Regulator Society of America,* Jul. 17–20, 1992.

Salajova et al., "Initiation of embryogenic tissues and plantlet regeneration from somatic embryos of *Pinus nigra* Arn," *Plant Science,* vol. 145, pp. 33–40, 1999.

Selby et al., "The influence of culture vessel head–space volatiles on somatic embryo maturation in Sitka spruce [*Picea sitchensis* (Bong.) Carr.]," *Plant Growth Regulation,* vol. 20, pp. 37–42, 1996.

Tautorus et al., "Somatic embryogenesis in conifers," *Canadian Journal of Botany,* vol. 69, No. 3, pp. 1873–1899, Sep. 1991.

Van Winkle et al., "Modeling Sorption of 2,4–D and BAP onto Activated Carbon," Abstract of The Eighth Meeting of The Conifer Biotechnology Working Group, Jun. 7–11, 1998, Modeling Sorption of 2,4–D and BAP Onto Activated Carbon.

Van Winkle, "The Impact of Activated Carbon on the Ionic and Hormonal composition of Plant Tissue Culture Media," Abstract, In–house seminar at Institute of Paper Science & Technology, Feb. 14, 2000.

Van Winkle, "Combined Effects of Activated Carbon and pH on Ionic Composition and 2,4–D Availability In A Tissue Culture Medium," Abstract, *Biological Sciences Symposium* 1997, pp. 49–56.

von Arnold, "Improved Efficiency of Somatic Embryogenesis in Mature Embryos of *Picea abies* (L.) Karst," *J. Plant. Physiol,* vol. 128, pp. 233–244, 1987.

Yang et al., "Effect of Brassinolide on Growth and Shikonin Formaton in Cultured *Onosma paniculatum* Cells," *J. Plant Growth Regulation,* vol. 18, No. 2, pp. 89–92, 1999.

* cited by examiner

METHODS OF INITIATING EMBRYOGENIC CULTURES IN PLANTS

CROSS REFERENCE TO RELATED APPLICATION

This application claims the benefit of priority under 35 U.S.C. § 119(e) of U.S. Provisional Application 60/212,651 filed Jun. 19, 2000, the disclosure of which is hereby incorporated by reference.

BACKGROUND OF THE INVENTION

Present invention provides methods for initiating embryogenic cultures of plants. These methods provide somatic embryos needed for reproducing large numbers of plants by somatic embryogenesis. More specifically, the invention encompasses various methods and media compositions that can improve the frequency of initiation of embryogenic cultures.

THE NEED FOR HIGH QUALITY TREES

The forest products industry is a major economic entity. In the United States the industry had sales of $400 billion dollars in 1994. Coniferous softwood species make up the majority of the trees harvested. In the Southeastern United States, Loblolly pine (*Pinus taeda* L.) and its close relatives are the most important species. In the Pacific Northwest, Douglas-fir (*Pseudotsuga menziesii* (Mirb.) Franco) is probably the most important commercial species. Likewise, in Europe, Norway spruce (*Picea abies* (L.) Karst.) is probably the most important conifer species.

Forest productivity can be increased by planting tree farms with large numbers of elite, high-quality trees. Unfortunately, trying to produce such trees by sexual reproduction yields seeds of unpredictable quality. Further, asexual reproduction by rooting vegetative cuttings, as is easily practiced with angiosperm species such as fruit trees, is not practicable for most coniferous species. What is needed is a method of clonally propagating large numbers of genetically superior conifer trees.

SOMATIC EMBRYOGENESIS

Plant tissue culture is the broad science of growing plant tissues on or in a nutrient medium containing minerals, sugars, vitamins and bioactive small molecules such as hormones. By adjusting the composition of the media, cultured tissues can be induced to grow or differentiate into specific cell types or organs. Somatic embryogenesis is a type of plant tissue culture where a piece of a donor plant is cultured such that an embryogenic culture is initiated. A proliferating embryogenic culture forms multiple embryos. An embryo is a discreet mass of cells with a well-defined structure that is capable of growing into a whole plant.

Somatic embryogenesis is widely used in a variety of species. In some species, somatic embryogenesis is used to propagate desirable plant genotypes. In many crop species, somatic embryogenesis is used to propagate tissues that have been genetically transformed, in order to regenerate whole transformed plants. Although somatic embryogenesis protocols are widely used and have been adapted to numerous species, most species include recalcitrant genotypes that are not readily regenerated. Further, some transformation methods, such as agrobacterium infection, electroporation and particle bombardment can damage plant cells and such damaged cells are not easily regenerated into whole plants. Thus, there is a need in the art for methods and compositions that can improve the efficiency of somatic embryogenesis in a wide variety of plant families.

Presently, somatic embryogenesis is seen as the most promising technology for the efficient multiplication of valuable coniferous germplasm. Since the late 1970's, researchers have been working to develop methods of reproducing conifers by somatic embryogenesis. U.S. Pat. Nos. 4,957,866, 5,034,326, 5,036,007, 5,236,841, 5,413,930 5,491,090, and 5,506,136, herein incorporated by reference, describe various methods and media for conifer embryogenesis.

INITIATION OF EMBRYOGENIC CULTURES

Culture initiation begins with the selection of a suitable explant, that is any plant cell, tissue or organ capable of forming an embryogenic culture. A typical explant in conifer somatic embryogenesis is the megagametophyte, also called the ovule or the female gametophyte, which is extracted from a pollinated female cone and which may contain single or multiple zygotic seed embryos. Next, an embryogenic culture is initiated from this explant by inducing cells within the explant to proliferate into a tissue mass containing at least one somatic early stage embryo. The successful establishment of such a culture is known as initiation.

Explants

Some conifer protocols known in the art use a megagametophyte that has been split open to expose the zygotic embryo or embryos. In one method, the embryo, while remaining attached to the megagametophyte by the long suspensor, is removed from the megagametophyte so that it is no longer surrounded by megagametophytic tissue. The embryo and attached megagametophyte are then both placed on a culture initiation media. In Douglas fir, for example, the embryo lies in a groove or channel within the megagametophyte. With careful manipulation, the embryo may be "flipped out" or displaced from the groove, yet ideally, remain attached to the megametophyte by the suspensor. Alternatively, the embryo or embryos may be completely separated from the megagametophye and placed on the media, either alone or next to the megagemetophytic tissue. The megagemetophytic tissue is often placed near the embryo, as it may produce growth regulators that promote initiation.

Extrusion

When intact conifer megagametophytes are used as the explant, the somatic embryogenesis process comprises a distinct step called extrusion. Prior to this distinct step in development of such megagametophytes, explants can be considered as pre-extrusion megagametophytes. Pre-extrusion therefore denotes the time before extrusion in such megagametophytes. Extrusion is the process in which a mass of embryogenic tissue is extruded from the micropylar end of the megagametophyte when it is placed on a suitable culture media. Becwar et al. (1990) observed in loblolly pine (*Pinus taeda*) that the extruded embryogenic tissue comes from cell division and proliferation in the suspensor region of the zygotic embryo or embryos. Extrusion can be observed using low power microscopy. The proliferation and growth of zygotic tissues pushes the embryogenic tissue out of the megagametophyte and it appears as a mass of filamentous suspensor-like cells containing single or multiple zygotic embryos. The mass sometimes contains dense globules that may be somatic proembryos or very early stage somatic embryos. Successful extrusion is scored whenever some tissue that has come outside of the intact megagametophytes via the micropyle is visible. Successful extrusion does not necessarily indicate that initiation will follow.

Typically, many of the extruded masses of tissue fail to proliferate and initiate an embryogenic culture.

Many conifer somatic embryogenesis protocols known in the art use intact megagametophytes as a preferred explant. However, prior to the discovery of the present invention, the entire initiation process including both extrusion and initiation, were carried out in a single media.

Initiation

Successfully initiating a high percentage of embryogenic cultures requires the proper medium and culturing conditions. In conifers, an embryogenic culture is successfully initiated when the zygotic embryo or zygotic embryogenic tissue mass, which has been either extruded or physically removed from a megagametophyte, undergoes division and proliferation. A successfully initiated culture will consist of a whitish translucent mucilaginous tissue mass that contains pre-embryonal masses of cells, filamentous suspensor-like cells and early stage somatic embryos. In a successfully initiated culture, new somatic embryos can often be seen growing directly from the somatic embryos. Visualization of initiation is aided by the fact that zygotic embryos, as well as extruded tissues, often become brown while initiated tissues are whiter and more translucent. Initiated cultures contain from one to dozens of somatic embryos. Initiation is considered successful when at least one somatic embryo is visible. The appearance of at least two somatic embryos provides a useful confirmation of successful initiation.

SUBSEQUENT STEPS TO REGENERATE WHOLE PLANTS

After embryogenic cultures are initiated, a number of subsequent steps are required to regenerate plantlets. First, the initiated somatic embryos are transferred to a multiplication or maintenance medium with the right composition of plant hormones and other factors to induce the somatic embryos to multiply at a high rate. Cultures can multiply as fast as 2–6 times weekly. Once large numbers of embryos are obtained in the multiplication stage, the embryos are moved to a maturation and development medium. Here, the correct balance of plant hormones and other factors will induce the early-stage embryos to mature into late stage embryos. Following the maturation and development stage, embryos are germinated to form small seedlings. These seedlings are then acclimated for survival outside of the culture vessel. After acclimation, the seedlings are ready for planting.

INITIATION MEDIA COMPONENTS

As noted above, protocols known in the art utilize a single media to induce the extrusion of embryogenic tissue and to initiate the proliferation of this tissue. The composition of the culture medium will determine the efficiency of plant regeneration by somatic embryogenesis. Several media constituents are known in the art to influence somatic embryogenesis in conifers.

Gelling Agent

The effect of gelling agents in plant tissue culture media has been investigated in various systems. Gelling agents are compounds that convert liquid media into solid or semi-solid colloidal suspensions. Increased amounts of gelling agent make the media more solid and decrease media matric potential, which is a measure of the ease with which water is extracted from the gel. One report suggests that the effect of matric potential on total media water status is negligible (Taito et al., 1999). Conversely, other reports suggest that changes in matric potential due to increased gelling agent have a significant effect on water availability, and thus affect the growth of cultured plant cells. For example, Ghashghaie et al. (1991) studied the effect of gelling agent concentration on shoot cultures of Rosa hybrida and found that water availability and shoot elongation increased with decreasing agar concentration. Similarly, Owens and Wozniak (1991) reported that increasing concentrations of gelling agent decreased gel matric potential and negatively affected somatic embryo and shoot growth. Etienee et al. (1991) observed that embryogenic culture initiation in rubber tree (*Hevea brasiliensis*) was increased using liquid media as opposed to gelled media.

Few studies have investigated the effects of the amount or composition of gelling agents in conifer embryogenic initiation media. VonArnold (1987) observed no effect of gel stiffness on initiation in *Picea abies*. Tremblay and Tremblay (1991), in two Picea species, compared gelling agents and obtained better initiation using GELRITE than comparable amounts of agar. Harry and Thorpe (1991) also found GELRITE to be superior to other gelling agents in initiating Red Spruce (*Picea rubens*) embryogenic cultures. None of these studies or other methods known in the art utilized initiation media with less than 1 g/l GELRITE or 4 g/l agar. For example, in U.S. Pat. No. 5,236,841, Gupta and Pullman disclose solid initiation media containing 6.0 and 7.0 g/l agar. Similarly, U.S. Pat. No. 5,413,930 and 5,506,136, herein incorporated by reference, disclose media using no less than 1 g/l GELRITE and 4 g/l agar.

As suggested above, all conifer embryogenic culture initiation methods known in the art utilize a solid initiation media. In contrast, liquid media are commonly employed in later culturing and regeneration steps. For example, in U.S. Patent 5,236,841, Gupta and Pullman disclose a method of regenerating coniferous plants by somatic embryogenesis that uses liquid maintenance and development media. Similarly, in U.S. Pat. No. 5,491,090, herein incorporated by reference, Handley et al. disclose a post-induction liquid media used to maintain embryogenic cultures.

While liquid media is used in later stages of conifer somatic embryogenesis, the use of liquid media in initiation media has not been suggested. Rather, conifer embryogenic initiation media known in the art contain sufficient gelling agents such as GELRITE, agar, gellan gum and agarose to produce a solid or semi-solid media.

The development of a liquid initiation media would be particularly advantageous as liquid media are more amenable to automation (Majada et al., 1991). Large scale germplasm screening and plant propagation will depend upon economical methods, and automation can reduce labor costs and increase the efficiency of somatic embryogenesis (Gupta et al., 1999).

Activated Charcoal

Activated charcoal or other adsorbent materials have been widely used in plant tissue culture media where they are believed to function as an adsorbent for toxic metabolic products and undesirable amounts of residual hormones. In one early report, Johansson (1983) measured embryogenesis in cultured anthers of ornamental plant species and utilized liquid media overlaying solid media that contained activated charcoal. He concluded that activated charcoal was effective in removing inhibitory amounts of ABA and other undesirable materials such as phenolics from the liquid media.

In conifer somatic embryogenesis, activated charcoal has been used in the development and maturation media. For example, U.S. Pat. No. 5,036,007, herein incorporated by reference, discloses a method of regenerating conifers using 2000 mg/l activated charcoal in the development media where early stage somatic embryos are matured. The use of activated charcoal in the initiation medium is also known. For example, U.S. Pat. Nos. 5,294,549, herein incorporated by reference, and U.S. Pat. No. 5,236,841, disclose initiation media containing 2500 mg/l activated charcoal.

Abscisic Acid

The use of abscisic acid (ABA) in culture media is known in the art of conifer tissue culture. Typically, ABA is used in the later stages of somatic embryogenesis following culture initiation. For example, Salajova et al. (1999), working with *Pinus nigra*, reports the use of ABA in the development media. Recently, it has been shown that ABA is also effective in aiding initiation of Pinus embryogenic cultures. U.S. Pat. No. 5,677,185, and U.S. Pat. No. 5,856,191, both herein incorporated by reference, disclose solid initiation media containing ABA and report initiation frequencies of 30-38% using media containing 30–90 mg/l ABA.

Silver Nitrate

Ethylene ($C_2H_4$) is a gaseous plant growth regulator that often accumulates during plant tissue culture. Ethylene is generally considered to depress the growth of cultured tissues. In conifers, however, some workers have observed that ethylene reduces the growth of cultured Picea embryogenic tissues (Kumar et al., 1989) while others have found no effect (Kvaalen, 1994). Several compounds, such as silver nitrate ($AgNO_3$) and cobalt chloride ($CoCl_2$), have been identified that block the action of ethylene.

The use of silver nitrate or other ethylene inhibitors is known in the art of conifer somatic embryogenesis but reports of its efficacy are mixed. Abdelmalek at al. (1999) tested the effects of silver nitrate on maturation of Black spruce (*Picea mariana*) somatic embryos and concluded that silver nitrate did not affect maturation and growth of the cultures, whereas Kong and Yeung (1995) obtained the opposite result in White spruce (*Picea glauca*). In Blue spruce (*Picea pungens*), Afele and Preveen (1995) observed that silver nitrate inhibited induction of embryogenic cultures. In contrast, Li and Huang (1996) observed that silver nitrate, at concentrations of about 29–59 $\mu$M improved embryogenic culture initiation in loblolly pine.

LOW INITIATION FREQUENCIES IN PINUS

In some varieties of conifer, methods exist for the efficient initiation of embryonic cultures. For example, a review by Tautorus et al. (1991) shows that numerous workers in the field have obtained Picea initiation frequencies over 50% and as high as 95%. In Norway Spruce (*Picea abies*), Chalupa (1997) obtained initiation frequencies of 52–96%.

Despite the success in propagating spruce (Picea) species and Douglas fir by somatic embryogenesis, the propagation of Pinus species is much more difficult. Many Pinus species, including Loblolly pine (*Pinus taeda*) do not readily initiate embryonic cultures. Typical initiation frequencies of about 1–12% are reported for various Pinus species (Becwar et al. 1988, Jain et al. 1989, Becwar et al. 1990 Li and Huang 1996). Laine and David (1990) however, were able to obtain high frequencies of initiation (up to 59%) in *Pinus caribaea*, suggesting that not all Pinus species are recalcitrant. Also, one earlier report described initiation frequencies of 54% in White pine (*Pinus strobus*) (Finer et. al, 1989). However, other workers were not able to duplicate this success (Michler et al., 1991). The results in the literature demonstrate the recalcitrance of Pinus species, especially Loblolly pine, in regeneration by somatic embryogenesis. One problem is that there is great variability among different genotypes in amenability to tissue culture. Consequently, regeneration potential can vary dramatically from tree to tree, and in open pollinated cones, from seed to seed even on a single tree. This complicates efforts to screen germplasm, because current methods used to regenerate plants for evaluation will select genotypes best able to survive the culturing process rather than a broad range of genotyopes.

Recently, some progress has been made in increasing initiation frequencies in recalcitrant Pinus species. Recent patents disclose improved methods of initiating embryonic cultures in Lobolly pine. U.S. Pat. No. 5,413,930, hereby incorporated by reference, describes the use of gelled initiation media to attain average initiation frequencies of 17%. U.S. Pat. No. 5,506,136, hereby incorporated by reference also discloses a method incorporating a gelled media and reports initiation frequencies of 15% and 50% in two different genotypes. U.S. Pat. No. 5,677,185 and U.S. Pat. No. 5,856,191, both hereby incorporated by reference, disclose solid initiation media containing abscisic acid (ABA) and report initiation frequencies of 30–38%.

Thus, there is a need in the art for further progress in the efficiency of culture initiation. There is a need in the art for a somatic embryogenesis method that yields high rates of initiation for multiple and diverse genotypes. Such high rates are important when selecting superior trees, the growth characteristics of many different genotypes, as trees growing in the field, must be evaluated. If one is attempting to propagate several genotypes and initiation frequencies are low, the majority of the material cannot be evaluated. Even assuming that desirable growth characteristics are not linked to embryonic culture potential, at initiation rates below 10%, over 90% of the desirable genotypes will be lost. Further, methods that select only the most easily propagated fraction of the population may actually select against other desirable traits.

There is a need in the art for an efficient somatic embryogenesis regeneration system for conifers and other plants to be used in conjunction with plant transformation techniques. The genes that control tree quality are currently being identified and characterized. In order to develop transgenic trees incorporating these genes, the existence of a reliable tissue culture and regeneration system is vital. Further, there is a need in the art for a regeneration system that can be automated for the large scale production of high-quality or transformed seedlings.

It is an object of this invention to provide novel methods to improve the efficiency of somatic embryogenesis in plants and, in particular, to provide efficient methods of initiating embryogenic cultures of diverse coniferous species and diverse genotypes within a species, specifically including diverse Pinus genotypes such as Loblolly pine (*Pinus taeda*). It is a further object to provide a method of somatic embryogenesis that will dependably and consistently provide coniferous plantlets in large quantities. It is yet another object to provide a general method of somatic embryogenesis that can dependably and consistently reproduce large numbers of clones of selected individuals of forest species that heretofore have been recalcitrant using known methods for somatic embryogenesis. It is still a further object to provide a method whereby superior genotypes of coniferous trees can be multiplied by tissue culture in the large quantities needed for reforestation. It is still a further object to provide a liquid media method that facilitates automation and large scale reproduction. It still another object to provide a method that generates robust somatic embryos capable of withstanding extended periods of cold storage or cryogenic preservation.

These and many other objects will become readily apparent to those skilled in the art by reading the following detailed description.

DETAILED DESCRIPTION OF THE INVENTION

The present invention is specifically directed to the use of various compositions and methods to improve the frequency of embryogenic culture initiation. The compositions and methods are particularly advantageous for the production of thousands of somatic embryos from multiple and diverse genotypes. The production of high numbers of somatic embryos aids in the efficient conversion of embryos into plants growing in soil. Thus, these methods allow the inclusion of more genotypes in subsequent clonal field tests and thereby increase the likelihood of being able to select highly productive genotypes. Further, some of the methods disclosed provide the art with a liquid initiation media, which allows the preliminary steps in somatic embryogenesis to be more easily automated and adapted to large scale production. In addition, use of these methods generates early stage embryos that can be retained for extended periods of time in cryogenic storage. Further, the methods interface very well with genetic engineering techniques for mass production of clones of genetically modified genotypes.

Several embodiments of the present invention are directed to the propagation of conifers. However, embodiments of the invention can be broadly applied to all plant families. As set forth below, these broadly applicable embodiments can increase the efficiency of embryogenic culture initiation in a wide variety of species and one of ordinary skill in the art will readily recognize the advantages of applying these compositions and methods to diverse plant families.

SPECIES AMENABLE TO THE INVENTION

Many embodiments of the present invention are generally suitable for reproducing woody gymnosperms of the order Coniferales. These are particularly well suited for generating clones of superior forest trees for reforestation, including species within the families Pinaceae, Cupressaceae, and Taxodiaceae. Most particularly, all species within the genera Abies, Pinus, Picea, Tsuga, Pseudotsuga, Thuja, Juniperis, Larix, Taxus and Sequoia are amenable to multiplication using the disclosed methods and compositions.

Some embodiments of the present invention are especially applicable to somatic tissue obtained from the Pinus species including, but not limited to, the following: *Pinus taeda* (loblolly pine), *Pinus elliottii* (slash pine), *Pinus palustris* (longleaf pine), *Pinus serotina* (pond pine), *Pinus radiata* (Monterey pine), and *Pinus rigida* (pitch pine). In addition, embodiments of the current invention are specifically applicable to hybrids (i.e., interspecies hybrids) of the above mentioned pines, including crosses between *Pinus rigida* and *Pinus taeda*, crosses between *Pinus serotina* and *Pinus taeda*, and reciprocal crosses.

Specific aspects of the invention are applicable to a broad number of plant families, including but not limited to the grass family (Poaceae), legumes (Fabaceae), plants from the mustard family (Brassicaceae), plants from the nightshade family (Solanaceae), the rose family (Rosaceae) and other plant families containing food, forest, forage, fiber or industrial crop species. For example, embryogenic culture initiation can be improved in important crops from the grass family, such as rice (*Oryza sativa*), corn (*Zea mays*) and wheat (*Triticum* spp.) using specific embodiments of the invention. Likewise, these embodiments can be applied to improve somatic embryogenesis in important legume crops such as soybean (*Glycine max*) or lentil (*Lens culinaris*).

SUITABLE EXPLANTS

Any plant tissue explant capable of being employed for somatic embryogenesis is suitable for use in the present invention. A number of explant sources have been used successfully in somatic embryogenesis. These include, but are not limited to, tissue from cotyledons, hypocotyls, epicotyls, buds, meristematic centers from buds or roots, tissues extruded from megagametophytes, and seed embryos. In conifers, one can use an immature whole megagametophyte containing zygotic embryos or an isolated immature dominant zygotic embryo as the explant. Zygotic embryos removed from seeds can be used. These may or may not include the surrounding gametophyte.

TWO STEP INITIATION

One embodiment of the invention comprises the use of separate media for extrusion and initiation. One aspect of this method comprises the use of a solid media upon which ovules are cultured until an optimal level of extrusion has occurred. At this point, a liquid initiation media is poured over the solid media and the extruded tissues are cultured until they have initiated embryogenic cultures. Alternatively, the extruded tissue may be removed from the extrusion media and placed in liquid initiation media.

MEDIA COMPOSITION

The processes of the present invention is not limited to any single culture medium. Any of a number of well known media, such as that of Murashige and Skoog (1962), may be used. However, the present inventors have found the basal medium described in Table 1 to give excellent results, particularly when used for culturing loblolly pine (*Pinus taeda*).

TABLE 1

Basal Solid and Liquid Initiation Media

| Components | (mg/l) Solid | Liquid |
|---|---|---|
| $NH_4NO_3$ | 200.0 | 200.0 |
| $KNO_3$ | 909.9 | 909.9 |
| $KH_2PO_4$ | 136.1 | 136.1 |
| $Ca(NO_3)_2$-$4H_2O$ | 236.2 | 236.2 |
| $MgSO_4$-$7H_2O$ | 246.5 | 246.5 |
| $Mg(NO_3)_2$-$6H_2O$ | 256.5 | 256.5 |
| $MgCl_2$-$_{6H2}O$ | 101.7 | 101.7 |
| KI | 4.15 | 4.15 |
| $H_3BO_3$ | 15.5 | 15.5 |
| $MnSO_4$-$H_2O$ | 10.5 | 10.5 |
| $ZnSO_4$-$7H_3O$ | 14.668 | 14.668 |
| $Na_2MoO_4$-$2H_2O$ | 0.125 | 0.125 |
| $CuSO_4$-$5H_2O$ | 0.1725 | 0.1725 |
| $CoCl_2$-$6H_2O$ | 0.125 | 0.125 |
| $AgNO_3$ | 3.398 | 3.398 |
| $FeSO_4$-$7H_2O$ | 13.9 | 13.9 |
| $Na_2EDTA$ | 18.65 | 18.65 |
| Maltose | 15,000 | 15,000 |
| myo-Inositol | 20,000 | 20,000 |
| Casamino Acids | 500 | 500 |
| L-Glutamine | 450 | 450 |
| Thiamine-HCl | 1.0 | 1.0 |
| Pyridoxine-HCl | 0.5 | 0.5 |
| Nicotinic acid | 0.5 | 0.5 |
| Glycine | 2.0 | 2.0 |
| NAA | 2.00 | 0.3 |
| BAP | 0.63 | 0.63 |
| Kinetin | 0.61 | 0.61 |
| Activated Charcoal | 50 | 50 |
| cGMP* | 10 uM | 10 uM |
| GELRITE | 2,000 | — |
| pH | 5.7 | 5.7 |

The extrusion or initiation medium will normally be one of those well known from past work which contains a balanced concentration of inorganic salts and organic nutrient materials. The media may contain plant hormones including auxins and cytokinins. What constitutes an effective amount of auxin or cytokinin will depend upon the species and the type of media used. For example, U.S. Pat. No. 5,565,355, herein incorporated by reference, discloses that *Pinus radiata* embryogenic cultures may be initiated in media that contains no auxin, cytokinin or other similar plant growth regulators. Therefore, an effective amount of auxin or cytokinin to be used in the invention can be zero. However, one can also incorporate auxin and cytokinin into the media of the present invention. Suitable levels for the present method include about 0.1 to 120 mg/l for auxin and about 0.1 to 100 mg/l for cytokinin.

The particular auxins and cytokinins used and their exact concentrations, or whether they are used at all, will depend somewhat on the species being cultured and even on the particular genotype within that species. For example, in Douglas fir, a suitable concentration of auxin is 110 mg/l and a suitable concentration of cytokinin is 88 mg/l. In solid media used for Loblolly pine, a suitable concentration of auxin is 2.0 mg/l and a suitable concentration of cytokinin is 1.24 mg/l. In liquid media used for Loblolly pine, a suitable concentration of auxin is 0.3 mg/l and a suitable concentration of cytokinin is 1.24 mg/l. The optimal amount to be used can be readily determined empirically by one of ordinary skill in light of the present disclosure. Of course, the optimal level of growth hormones also depends on the presence or absence of an adsorbent material, such as activated charcoal. Activated charcoal can adsorb a large proportion of free auxins and cytokinins, requiring the addition of higher levels to compensate. Finally, it will be understood by those skilled in the art that analogs and similar plant hormones may be substituted for the auxins and cytokinins listed below in Table 2.

TABLE 2

Common Auxins and Cytokinins Used in Plant Tissue Culture

| Abbreviation | Compound |
|---|---|
| Auxins | |
| 2,4-D | 2,4-dichlorophenoxyacetic acid |
| NAA | 2-Naphthylacetic acid |
| IAA | indole-3-acetic acid |
| IBA | indole-3-butyric acid |
| Cytokinins | |
| BAP | N6-benzylaminopurine (or N6-benzyladenine) |
| KIN | kinetin (6-furfurylaminopurine) |
| 2-IP | N6-isopentenylaminopurine |
| — | zeatin |

The media should contain a readily metabolized carbohydrate energy source, like a sugar such as maltose, glucose, fructose, sucrose, or galactose, or combinations thereof. One may utilize a wide range of sugar concentrations, such as between 5 and 70 g/l. Maltose is an effective carbohydrate source. Several embodiments of the present invention utilize media containing maltose at a concentration of 15 g/l.

GELLING AGENT

If a solid, semi-solid or viscous initiation media is desired, gelling agents can be added to the initiation medium. For example, the use of 2.5 to 8 g/l of agar, 0.5 to 5.0 g/l of gellan gum, 3.0 to 8.0 g/l of agarose will yield a semi-solid to solid media, with gel stiffness increasing as the level of gelling agent is increased. Several embodiments of the present invention utilize solid media containing 2.0 g/l gellan gum.

An improvement of the present invention is the use of an initiation media that contains little or no gelling agent. Indeed, heretofore no one has shown that using completely liquid media in conifer embryogenic culture induction is effective in initiating conifer embryogenic cultures. Some embodiments of the present invention comprise the use of a liquid initiation media containing from about 0.0–2.5 g/l agar, 0.0–0.5 g/l gellan gum, 0.0–3.0 g/l agarose or 0.0–1.5 g AGARGEL, including any concentration of agar, gellan gum, agarose or AGARGEL subscribed by the recited ranges. Irrespective of its composition, a liquid initiation media is considered liquid, within the scope of the invention, if an explant does not remain on the surface of the media throughout normal culture conditions. Alternatively, a liquid media is hereby defined as one which can be poured into a culture vessel and form a substantially level surface (disregarding the meniscoid effects of surface tension) at 20° C. One embodiment of the liquid initiation media contains no gelling agent at all.

It will be understood by those skilled in the art that the gelling agents listed above are representative and that the use of equivalent substitutes falls within the scope of the invention. Further, the invention encompasses the combination of different gelling agents such that the desired solid, semi-solid or liquid media is formed.

ACTIVATED CHARCOAL

This invention improves on the prior art by teaching the use of reduced levels of activated charcoal in the extrusion and the initiation media. Conifer somatic embryogenesis methods known in the art utilize much larger amounts of activated charcoal. For example, U.S. Pat. Nos. 5,294,549 and 5,236,841 disclose initiation media containing 2500 mg/l activated charcoal. High initiation frequencies can be attained using less than 2500 mg/l, for example, between about 10 to 2000, 10 to 650, or 100 to 500 mg/l of activated charcoal, or any concentration subsumed within those ranges. Activated charcoal may be used in either liquid or solid media. An effective activated charcoal concentration for Loblolly pine initiation is about 10 to about 100 mg/l. A concentration of 25 to 75 mg/l may be used. Several embodiments of the invention employ a concentration of 50 mg/l. Several embodiments of the initiation media used for Norway spruce contain 200 to 400 mg/l activated carbon. A concentration of 250 to 350 mg/l may be used. One embodiment of the invention utilizes a concentration of 300 mg/l. Those skilled in the art will recognize that other adsorbent materials may be substituted for activated charcoal, including other forms of activated carbon.

Activated charcoal adsorbs large amounts of copper and zinc in the media, and this depletion may result in deficiencies. The depletion of zinc and copper caused by activated charcoal can be compensated by the addition of extra zinc and copper. Working with multiple conifer species, we have discovered that when copper and zinc are added to the media to compensate for the adsorbed ions, the growth of embryonic cultures is enhanced. A suitable level of anhydrous $ZnSO_4$ is 14.7 mg/l in a liquid media containing 50 mg/l activated charcoal. A suitable level of anhydrous $CuSO_4$ is 0.17 mg/l in a liquid media containing 50 mg/l activated charcoal. Those skilled in the art will recognize that several alternative sources of zinc and copper may be substituted for those suggested above.

ABSCISIC ACID (ABA)

The present invention comprises novel methods of using abscisic acid (5-(1-hydroxy-2,6,6,-trimethyl-4-oxo-2- cyclohexen-1-yl)-3-methyl-2,4-penta dienoic acid) (ABA) to improve induction of embryogenic cultures. In one embodiment, explants are pre-treated for several minutes up to overnight with an aqueous solution of abscisic acid prior to culturing with an initiation media that lacks ABA. The duration of the pre-culturing soak and the concentration of ABA to be used in the soaking solution may vary with the type of explant used and the permeability of the explant to the solution, and explants may be rinsed with media lacking ABA prior to culturing. Several methods of the current invention utilize ovules excised from conifer seeds. In one embodiment, the ovules are soaked in water, buffer or liquid media containing from 1–50 parts per million (ppm) ABA. Some embodiments of the invention utilize a concentration of 10–20 ppm ABA in the soaking solution. Some embodiments of the pre-treatment method utilize a soaking duration of one to 80 minutes. Alternatively, one can pre-treat for 15 to 120 minutes or 30 to 45 minutes.

Several embodiments of the invention employ a liquid media containing ABA. When liquid initiation media is used, the media can contain from 0.01 to 1 mg/l ABA. In one embodiment of the liquid media, the media contains from 0.05 to 0.15 mg/l ABA. Some embodiments of the liquid media contain 0.1 mg/l ABA. In contrast, in some embodiments of the invention, the media is substantially free of ABA, meaning that ABA is effectively absent from the media formulation. In such embodiments, ABA is not present at all, or is present in insignificant amounts, such that plant growth in such media is indistinguishable from growth in the complete absence of ABA.

Liquid initiation media containing ABA can be used in numerous ways. In one embodiment of the invention, all culturing takes place in a liquid medium containing ABA. In a separate embodiment, the invention comprises the use of liquid initiation media containing ABA to initiate embryogenic cultures from tissue that has been previously extruded on a separate extrusion media containing little or no ABA. In various embodiments of this method, the extrusion media contains less than 0.1 mg/l ABA, less than 0.01 mg/l ABA, or is completely lacking ABA (0.00 mg/l). Extrusion occurs on this media. After extrusion has occurred, a liquid media containing ABA is poured over the extruded tissue or the tissue is removed from the solid media and placed in the liquid media. It will be recognized by those skilled in the art that ABA can have physiological effects at very low concentrations. It will also be recognized by those skilled in the art that the method of ABA application, such as vacuum filtration, soaking or physical contact with culture media, will affect the ABA concentration experienced by the explant. Further, the ABA delivery media, whether it is solid media, liquid media or buffer, will also affect the concentration experienced by the explant. Additionally, the presence of an adsorbent material such as activated carbon can greatly reduce the amount of free ABA such that additional ABA must be added to the medium to compensate. Therefore, it is understood that what constitutes an effective amount of ABA will depend on the method of application and media composition. Using the methods disclosed in the Examples, one of skill in the art can readily determine empirically what will constitute an effective amount for each protocol. Further, it will be understood by those of skill in the art that the invention encompasses the use of analogs and variants of ABA.

SILVER NITRATE

One aspect of the present invention is the use of sliver nitrate ($AgNO_3$) in the extrusion and initiation media. It is known in the art that silver nitrate decreases the action of ethylene and can have significant effects in plant tissue cultures. The use of silver nitrate in conifer embryogenic culture initiation media is known. However, there are conflicting results in the art as to whether it improves or inhibits somatic embryogenesis in conifers. Nevertheless, our results indicate that silver nitrate improves embryogenic culture initiation. Those skilled in the art will recognize that other ethylene inhibitors such as silver thiosulfate ($[Ag(S_2O_3)_2]^{3-}$) or cobalt chloride ($CoCl_2$) may be substituted for silver nitrate. Silver nitrate may be used in liquid or solid media, at concentrations ranging from 1–50 µM. When silver nitrate is used in a liquid media concentrations of 10–20 µM, or about 2–4 mg/l are effective.

BRASSINOSTEROIDS

This invention improves on the plant tissue culture art by teaching the novel use of brassinosteroids in somatic embryogenesis. We have discovered that brassinosteroids can be used to promote initiation of embryogenic cultures. The brassinosteroids are a group of naturally occurring steroidal lactones which include brassinolide and its analogs. The brassinosteroids were relatively recently discovered to be plant growth regulators. In angiosperm species, brassinosteroids have been shown to have diverse, tissue-specific and species-specific effects, including the stimulation of cell elongation, stimulation of ethylene production and increasing resistance to abiotic stress (Brosa, 1999). Brassinolide is a brassinosteroid found in many plant species. The formula of brassinolide is:

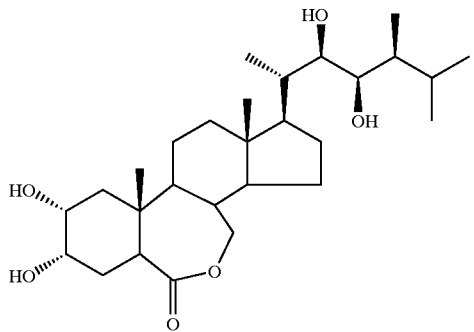

Brassinolide analogs are known in the art. For example, U.S. Pat. No. 5,965,488, herein incorporated by reference, discloses the following general formula for brassinolide analogs:

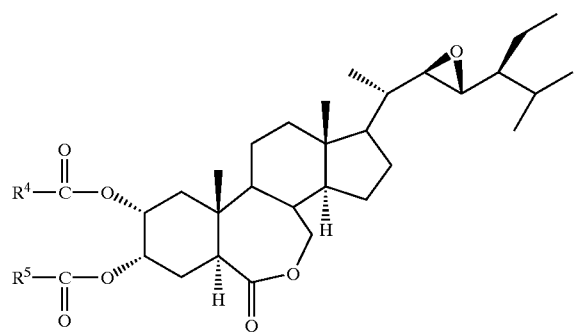

wherein $R_4$ and $R_5$ are $C_1$–$C_6$ lower alkyl groups. The $C_1$–$C_6$ alkyl groups represented by $R_4$ and $R_5$ are preferably $C_1$–$C_4$ straight-chain alkyl groups and include a methyl group, ethyl group, propyl group and butyl group. In particular, the ethyl group and propyl group are preferable for high activity.

Naturally occurring brassinosteroids have been isolated from conifers (Kim et al., 1990). Brassinosteroids have been applied exogenously to pine seedlings (Sasse et al., 1992) and spruce cuttings (Ronsch et al., 1993) and have been found to promote root growth. Nevertheless, the use of brassinosteroids in conifer tissue culture has not been previously reported. In fact, the effects of brassinosteroids on cultured plant cells of any species has not been extensively investigated. In one of the few reports available on the effects of brassinosteroids in tissue culture, Yang et al. (1999) found slightly increased growth of cultured cells of Onosma paniculatum (an angiosperm species used as an herbal medicine) in media containing 0.01 ppb brassinolide. Conversely, Roth et al. (1989) observed that brassinosteroids inhibited the growth of cultured tobacco cells. Both of these reports dealt with non-embryogenic cell cultures. The use of brassinosteroids in somatic embryogenesis has not been reported.

As noted above, heretofore no one has explored the efficacy of brassinosteroids at any stage of the somatic embryogenesis process, for any species. Consequently, heretofore no one even suggested that using brassinosteroids is highly advantageous in initiating embryogenic tissue cultures. This invention thus comprises the use of brassinosteroids in somatic embryogenesis, in any species, including conifers. The use of brassisteroids could potentially be employed in somatic embryogenesis of Conifer species within the genera Abies, Pinus, Picea, Tsuga, Pseudotsuga, Thuja, Juniperis, Larix, Taxus and Sequoia. Additionally, brassinosteroids can be used in somatic embryogenesis of species in important families such as Poaceae, Fabaceae, Brassicaceae, Solanaceae, Rosaceae, and other plant families containing food, forest, forage, fiber or industrial crop species.

The present invention comprises the use of brassinosteroids in liquid or solid initiation media. Additionally, in conifers, brassinosteroids can be used in extrusion media. The results of our experiments showed that brassinolide has a positive effect on the initial proliferation of embryogenic tissues in plants. In our media, brassinolide was effectively used in concentrations ranging from 0.005–0.25 $\mu$M. However, it will be recognized by those skilled in the art that the presence of adsorbent materials such as activated carbon can potentially reduce the amount of free brassinolide available to cultured tissues. Thus, the concentration that represents an effective amount of brassinolide will depend upon the media composition, as well as the form of the media (liquid vs. solid) as well as the method of application. Using the Examples disclosed in this application, one of skill in the art can readily determine what constitutes an effective amount of brassinosteroid in a specific media. One embodiment of the invention comprises a liquid media containing about 0.10 $\mu$M brassinolide. It will be recognized by those skilled in the art that other brassinosteroids, including brassinolide analogs, may be substituted for brassinolide, for example those disclosed in U.S. Pat. No. 5,965,488, which is herein incorporated by reference.

ATMOSPHERIC PRESSURE

Numerous studies have focused attention on the composition of the atmosphere within plant tissue culture vessels. Consequently, it is known in the art that the composition of the atmosphere within culture vessels can have significant effects on somatic embryogenesis. Cultured cells deplete oxygen, and produce carbon dioxide and ethylene, which can accumulate in the headspace above the media in covered culture vessels. The effects of these atmospheric changes have been studied in several species, including conifers. For example, in Picea abies, Kvaalen and von Arnold (1991) observed that a low oxygen atmosphere stimulated the initiation of embryogenic cultures when full strength media was used, and inhibited initiation when half strength media was used. Selby et al. (1996) studying Sitka spruce (Picea sitchensis), determined that removing volatile compounds from the atmosphere of the culture vessel stimulated embryo maturation. Abdelmalek et al. (1999) observed that Picea mariana embryogenic cultures had better maturation rates in unvented containers than vented containers, and ruled out ethylene accumulation as causing this effect.

Despite the attention given to the composition of environmental gasses, the effect of increased atmospheric pressure on cultured cells has not been widely investigated in plants. This is unlike the situation in animal tissue culture, where the effects of hydrostatic pressure on various cell types has been extensively studied; usually the pressure is applied to simulate mechanical stress in the cells' normal environment and to measure effects on factors such as gene expression or cell differentiation. In the field of plant tissue culture, only a single reference describes the effects of culturing cells in a pressurized environment. Specifically, Barthou et al. (1997) studied sunflower (Helianthus annuus L.) protoplasts cultured for 7 days at 2–6 times normal atmospheric pressure. Barthou reported a generally adverse effect on cell growth, observing that pressures above 4 atmospheres inhibited cell division and microtubule synthesis. Thus, the sole reference in the field teaches away from the use of increased pressure in plant tissue culture.

The present invention improves the art of plant tissue culture by teaching the use of elevated atmospheric pressure in somatic embryogenesis. As noted above, heretofore no one has explored the efficacy of using increased atmospheric pressure at any stage of somatic embryogenesis. Indeed, heretofore no one has shown or even suggested that using increased atmospheric pressure is highly advantageous in initiating embryogenic tissue cultures. The results of our experiments showed that increased atmospheric pressure within the culture vessel has a profound effect on the initial proliferation of embryogenic tissues in plants. Our experiments also showed that increased atmospheric pressure increases the extrusion of embryogenic tissues in conifers. The improvement of the present invention comprises culturing embryogenic tissue, using either liquid, semi-solid or solid initiation media, and increasing the atmospheric pressure of the culture environment to above normal pressure (>1 atm) for all or part of the initiation period. Our results demonstrate that the pressure effect does not depend on continuous pressure. Occasional depressurization so that culture dishes can be observed does not appear to diminish the beneficial pressure effect. In one embodiment, increased atmospheric pressure is applied during the entire extrusion and initiation process. In other embodiments, increased pressure is applied for at least one week, or from 2 to 14 weeks, or from 3 to 10 weeks. In one embodiment the pressure ranges from 1.1 to 5.0 atmospheres. In another embodiment the pressure is 1.3 to 1.7 atmospheres. In yet another embodiment, the pressure is 1.5 atmospheres. As used herein, 1 atmosphere is generally equivalent to about 1013 millibar, however, the increased pressure range of the invention may also be calculated as pressure in excess of ambient atmospheric pressure.

INITIATION CONDITIONS

Culturing during the extrusion or initiation stage may be carried out in the dark, under very low light conditions, or in full light until an embryogenic mass forms. In general, initiation in full dark is preferred. Culture initiation lasts for a period of from about 2 to 14 weeks. In another embodiment the culture period is from 3–10 weeks.

The media within a vessel may be replaced. Occasionally, a culture that has initiated and contains somatic embryos will not proliferate vigorously. If such a culture is in liquid media, the addition of fresh liquid media may promote growth and lead to more vigorous initiation. Alternatively, if such a culture is on solid media, the tissue can be moved to new solid media in a different vessel or can be moved to a new location in the same vessel. One of skill in the art will recognize that the methods of the invention can be carried out wherein old media is periodically replaced with fresh media of the same composition.

TERMS AND DEFINITIONS

A number of terms are known to have differing meanings when used in the literature. The following definitions are believed to be the ones most generally used in the field of botany and are consistent with the usage of the terms in the present specification.

"Auxins" are plant growth hormones that promote cell division and growth.

"Corrosion cavity" is the cavity within the megagametophyte tissue of conifers formed by the growth and enlargement of the zygotic embryos.

A "cotyledonary embryo," sometimes simply referred to as an "embryo," has a well defined elongated bipolar structure with latent meristematic centers having clearly visible cotyledonary primordia surrounding and usually obscuring an apical dome at one end and a latent radicle at the opposite end. The cotyledonary structure frequently appears as a small "crown" at one end of the embryo. A cotyledonary somatic embryo is analogous to a zygotic embryo.

"Cryopreservation" refers to the common process of storing cultures at ultra-low temperatures for future use.

"Cytokinins" are plant growth hormones that affect the organization of dividing cells.

An "Embryo," depending on its stage of development, will have a variable morphology. Stages 1–9.10 as defined by Pullman and Webb, TAPPI R&D Division 1994 Biological Sciences Symposium, pp 31–34, which is hereby incorporated by reference, define embryos at different points of development. Development spans from Stage 1, where embryos are composed of 12 or less cells to Stage 9.10 where embryos are well developed and have accumulated their full mature weight.

"Embryogenic tissue" in Conifers is a translucent white mucilaginous mass that contains early stage embryos and suspensor-like cells, and may contain small, dense globular clusters of cells capable of forming somatic embryos.

An "explant" is the organ, tissue, or cells derived from a plant and cultured in vitro for the purpose of starting a plant cell or tissue culture.

"Extrusion" is the process by which zygotic embryos and/or embryogenic tissue derived from zygotic embryos emerges or extrudes from the corrosion cavity of the megagametophyte of conifer seeds via the opening in the micropylar end, when placed in culture.

"Genotype" is the particular genetic composition of an organism.

"Initiation" is the initial cellular proliferation and development of zygotic tissues to form a culture containing somatic embryos.

A "megagametophyte" is haploid nutritive tissue of the conifer seed, of maternal origin, within which the conifer zygotic embryos develop.

A "micropyle" is the small opening in the end of the conifer seed from which zygotic and/or embryogenic tissue extrudes from the megagametophyte when cultured.

"Nutrients" are the inorganic nitrogen, inorganic minerals, vitamins, organic supplements, and carbon sources necessary for the nourishment of the culture.

A "plantlet" is a small germinating plant asexually reproduced by tissue culture.

A "somatic embryo" is a vegetatively produced embryo formed during culturing.

"Somatic embryogenesis" is the process using tissue culture techniques for generating multiple embryos from an explant. The embryos generated from a given tissue source are believed to be genetically identical.

A "suspensor cell" is an elongated and highly vacuolated filamentous cell.

A "zygotic embryo" is an embryo(s) which is derived from the sexual fusion of gametes during pollination and is found within the megagametophyte.

The present invention is illustrated by the following Examples, which are not intended to be limited in any way.

EXAMPLES

Example 1

Norway Spruce Initiation in Liquid Media

This experiment demonstrates the efficacy of a liquid initiation medium compared to a solid initiation medium in Norway spruce. The two initiation media used were based on solid media #56 (see Table 3). Liquid media #403 was identical in composition except that it contained no agar gelling agent.

The explants in this experiment were isolated from wild seeds. Seeds were sterilized as follows. Seeds were soaked in running water for 10 minutes, and then agitated in 10% liquinox plus about 5 ml TWEEN 20 per liter, for 10 minutes. Seeds were rinsed with running tap water for 30 minutes. In a sterile hood, the seeds were agitated for ten minutes in 10% $H_2O_2$ (hydrogen peroxide), rinsed with sterile deionized water 5 times and placed in sterile petri plates for dissection. Seeds were then soaked overnight. Seeds were then split and megagametophytes removed.

The explants used in this experiment were excised cotyledonary (mature) zygotic embryos. To obtain the embryos, the megagametophytes were split and the embryos were removed from inside each megagametophyte. The embryo and megagametophyte were then placed next to each other either in or on the media.

The composition of the solid and liquid media are described in Table 3. Each media treatment consisted of three replications. Replicates consisted of ten petri dishes, each containing 10 ml of media. The #56 solid media was poured into culture dishes right after autoclaving, while still liquid, and became solid upon cooling to room temperature. An inert 1.5×1.5 inch polyester pad was placed in the dishes containing liquid media #403 to minimize drifting and to keep the explants partially submerged in the media. A black filter paper disc was placed on top of the polyester pad to improve visualization of the explants. One explant was placed in each dish, directly on the media in the solid treatment and on top of the filter paper and pad, partially submerged, in the liquid treatment. The dishes were wrapped in PARAFILM and incubated at 23–24° C. under lighted conditions.

After nine weeks of culturing, each dish was examined and initiation frequency was measured as the number of successfully initiated cultures per ten explants. A successful initiation was scored where a proliferation of embryogenic tissues containing somatic embryos was clearly observed. In Norway spruce, embryogenic culture initiation occurs mostly on the hypocotyl region of the excised zygotic embryo. As is evident in Table 4, the percentage of explants successfully initiating an embryogenic culture was higher in liquid media #403.

TABLE 3

Norway Spruce Initiation Media #56 and #403

| Components | Solid (#56) (mg/l) | Liquid (#403) (mg/l) |
|---|---|---|
| KCl | 372.5 | 372.5 |
| $KNO_3$ | 50 | 50 |
| $KH_2PO_4$ | 85 | 85 |
| $MgSO_4$-$7H_2O$ | 160 | 160 |
| $CaCl_2$-$6H_2O$ | 220 | 220 |
| KI | 0.145 | 0.145 |
| $H_3BO_3$ | 3.1 | 3.1 |
| $MnSO_4$-$H_2O$ | 8.45 | 8.45 |
| $ZnSO_4$-$7H_2O$ | 4.3 | 4.3 |
| $Na_2MoO_4$-$2H_2O$ | 0.125 | 0.125 |
| $CuSO_4$-$5H_2O$ | 0.0125 | 0.0125 |
| $CoCl_2$-$6H_2O$ | 0.0125 | 0.0125 |
| $FeSO_4$-$7H_2O$ | 13.9 | 13.9 |
| $Na_2EDTA$ | 18.65 | 18.65 |
| Sucrose | 10,000 | 10,000 |
| myo-Inositol | 50 | 50 |
| Casamino acids | 500 | 500 |
| L-Glutamine | 750 | 750 |
| Thiamine-HCl | 0.05 | 0.05 |
| Pyridoxine-HCl | 0.05 | 0.05 |
| Nicotinic acid | 0.25 | 0.25 |
| L-Asparagine | 50 | 50 |
| NAA | 2.0 | 2.0 |
| BAP | 1.0 | 1.0 |
| Difco © Agar | 7,000 | — |
| pH | 5.8 | 5.8 |

TABLE 4

Norway Spruce Initiation Frequency
Initiation Frequency (% of explants successfully initiating embryogenic culture)

| Treatment | Mean + (Standard Error) |
|---|---|
| Solid Media (#56) | 23.3 (8.8) |
| Liquid Media (#403) | 48.0 (7.5) |

Example 2

Douglas Fir Initiation in Liquid Media

The purpose of this experiment was to demonstrate the efficacy of liquid initiation medium (#499) compared to solid media #121 in Douglas fir. The two initiation media were identical in composition, except that solid media #499 contained 2.0 g/l GELRITE brand gellan gum and liquid media #499 contained no gelling agent (Table 5).

The explants used in this experiment were stage 3–5 (early-midstage) zygotic embryos. The explants in this experiment were isolated from Douglas fir cones collected in early July. Seeds were sterilized as described in Example 1 above for Norway spruce. The sterilized seeds were split open and the megagametophytes removed. The megagametophytes were split and the embryos were carefully removed from inside each megagametophyte such that they remained attached to the megagametophyte by the long suspensor cells. The embryo and attached megagametophyte were then placed next to each other in or on the media.

The composition of the solid media #121 and liquid media #499 are described in Table 5. Each media treatment consisted of three replications. Replicates consisted of 9 cm petri dishes, each containing 10 ml of media. The solid media treatment was poured into culture dishes while still liquid and became solid upon cooling to room temperature. An inert 1.5×1.5 inch polyester pad was placed in the dishes containing liquid media to minimize drifting and to keep the explants partially submerged in the media. A black filter paper disc was placed on top of the polyester pad to improve visualization of the explants. Ten explants were placed in each dish, on the media in the solid treatment and on top of the filter paper and pad in the liquid treatment. Ten explants were placed in each dish. The dishes were wrapped in PARAFILM and incubated at 23–24° C. in the dark.

TABLE 5

Douglas Fir Initiation Media Composition

| Components | Solid (#121) (mg/l) | Liquid (#499) (mg/l) |
|---|---|---|
| $KNO_3$ | 1250 | 1250 |
| $CaCl_2$-$2H_2O$ | 200 | 200 |
| $KH_2PO_4$ | 340 | 340 |
| $MgSO_4$-$7H_2O$ | 400 | 400 |
| KI | 1.0 | 1.0 |
| $H_3BO_3$ | 5.0 | 5.0 |
| $MnSO_4$-$H_2O$ | 208 | 20.8 |
| $ZnSO_4$-$7H_2O$ | 8.0 | 8.0 |
| $Na_2MoO_4$-$2H_2O$ | 0.2 | 0.2 |
| $CuSO_4$-$5H_2O$ | 0.025 | 0.025 |
| $CoCl_2$-$6H_2O$ | 0.025 | 0.025 |
| $FeSO_4$$7H_2O$ | 27.8 | 27.8 |
| $Na_2EDTA$ | 37.3 | 37.3 |
| Sucrose | 15,000 | 15,000 |
| myo-Inositol | 1,000 | 1,000 |
| Casamino acids | 500 | 500 |
| Thiamine-HCl | 1.0 | 1.0 |
| Pyridoxine-HCl | 0.5 | 0.5 |
| Nicotinic acid | 0.5 | 0.5 |
| Glycine | 2.0 | 2.0 |
| 2,4-D | 110 | 110 |
| BAP | 45 | 45 |
| Kinetin | 43 | 43 |
| Activated Charcoal | 2,500 | 2,500 |
| GELRITE | 2,000 | — |
| pH | 5.7 | 5.7 |

After nine weeks of culturing, each dish was examined and initiation frequency was measured as the number of successfully initiated cultures per ten explants. A successful initiation was scored where a proliferation of embryogenic tissues containing somatic embryos was clearly observed. The embryogenic tissue tended to proliferate from the head region of the zygotic embryo. Initiation frequency, which is the percentage of explants induced to form embryogenic cultures, was higher in liquid medium #499 (Table 6).

TABLE 6

Douglas Fir Initiation Frequency
Initiation Frequency (% of explants successfully initiating embryogenic culture)

| Treatment | Mean + (Standard Error) |
|---|---|
| Solid Media (#121) | 44% |
| Liquid Media (#499) | 56% |

Example 3

Liquid Initiation Media for Loblolly Pine

In this experiment, Loblolly pine embryogenic tissue extrusion and culture initiation was tested in media containing a range of very low gelling agent concentrations. The experiment demonstrates the efficacy of using a liquid initiation media and also shows that wholly immersed explants can initiate embryogenic cultures. All treatment media contained a low level of gelling agent or no gelling agent at all, were liquid, and could be easily poured at room temperature. In all but one treatment, the full immersion treatment, a black felt pad, supported by an inert sorborod plug, was used to support the explant so that it was only partially submerged in the media. As zygotic and embryogenic tissues are whitish and translucent, the use of a felt support allowed easier visualization of the extruded tissues and somatic embryos.

The source of seeds in this experiment were from collections of open pollinated summer cones from four individual trees. Each tree was a distinct genotype. The use of diverse seed sources allowed the efficacy of the method across a range of genotypes to be tested. This is especially important in Pinus species where there is great variability among genotypes in amenability to somatic embryogenesis. Zygotic embryos from these cones were Stage 2–4 embryos.

The explants in this experiment were whole megagametophytes. Megagametophytes were obtained as follows. Seeds were sterilized as described in Example 1. Seed coats were split and the megagametophytes were isolated by removing integuments and nucellar tissue. Culturing was done in 24-well multiwell culture plates with each well having an approximate volume of 3.0 ml. Two ml of media was poured into each well. In all but one treatment, the explants were partially submerged in the media by placing them on black filter paper discs, supported by felt supports. In one treatment the explants were totally immersed in the media. All treatment media were based on liquid media #1038. The composition of media #1038 is described in Table 43 and treatment media compositions are described in Table 7. There were three replications per treatment, per genotype. Each replication consisted of ten megagametophytes, contained in ten adjacent wells on a culture plate. The plates were wrapped in PARAFILM and incubated at 23–24° C. in the dark.

After 8 weeks, the megagametophytes were observed to determine the frequency of extrusion. In each replicate set of ten explants, the frequency of extrusion was measured as the number of extrusions per ten megagametophytes. A successful extrusion was scored where a filamentous mass of tissue that had emerged from the megagametophyte was clearly visible. Extrusion frequencies in the different treatments are summarized in Table 8. Initiation was also scored at the end of the $8^{th}$ week. In each replicate set of ten explants, the frequency of initiation was recorded as the number of successful initiations out of the ten megagametophytes. A successful initiation was scored where the extruded tissue had clearly proliferated and at least one somatic embryo was visible. Often, visualization was aided by the fact that the zygotic tissue was brownish while new somatic embryos were whitish and translucent. Also, somatic embryos could often be seen growing directly from zygotic embryos. The initiation frequencies are summarized in Table 9.

Extrusion averaged over 30% in all treatments. Initiation frequencies exceeded 10% in all treatments, except media #1075, which contained the most gelling agent. The highest initiation rates were observed in the fully immersed ovule treatment (18.5%). These results illustrate that a liquid media can be used effectively to initiate embryogenic cultures in Loblolly pine. Importantly, the results suggest that full immersion in liquid media is not detrimental to the culturing process and may actually increase initiation compared to partial immersion of explants.

The results also illustrate the wide genetic variability in amenability to somatic embryogenesis among various pine genotypes. Not a single megametophyte from the 5–1056 genotype initiated a culture in any treatment, in contrast to the H5 genotype where initiation averaged over 25%.

TABLE 7

Treatment Media Compositions and Immersion

| Treatment # | Media | Immersion |
|---|---|---|
| 1 | Basal Media (#1038) | Partial |
| 2 | Media #1073 (Basal Media #1038 + 100 mg/l GELRITE) | Partial |
| 3 | Media #1059 (Basal Media #1038 + 200 mg/l GELRITE) | Partial |
| 4 | Media #1074 (Basal Media #1038 + 300 mg/l GELRITE) | Partial |
| 5 | Media #1075 (Basal Media #1038 + 400 mg/l GELRITE) | Partial |
| 6 | Media #1059 (Basal Media #1038 + 200 mg/l GELRITE | Full |

TABLE 8

Extrusion Frequencies
% of Megagametophytes Extruding - Mean (Standard Error) Genotype

| Treatment | 5-1056 | 21-6 | 5-1036 | H5 | Total |
|---|---|---|---|---|---|
| #1 (no gelling agent) | 6.7 (3.3) | 33.3 (6.7) | 36.7 (3.3) | 53.3 (8.8) | 32.5 |
| #2 (100 mg/l GELRITE) | 20.0 (10.0) | 60.0 (20.8) | 30.0 (5.8) | 33.3 (16.7) | 35.82 |
| #3 (200 mg/l GELRITE) | 10.0 (5.8) | 36.7 (8.8) | 36.7 (14.5) | 70.0 (5.8) | 38.35 |

TABLE 8-continued

Extrusion Frequencies
% of Megagametophytes Extruding - Mean (Standard Error) Genotype

| Treatment | 5-1056 | 21-6 | 5-1036 | H5 | Total |
|---|---|---|---|---|---|
| #4 (300 mg/l GELRITE) | 36.7 (8.8) | 53.3 (8.8) | 26.7 (14.5) | 70.0 (5.8) | 46.68 |
| #5 (400 mg/l GELRITE) | 3.3 (3.3) | 46.7 (3.3) | 30.0 (5.8) | 36.7 (12.0) | 29.18 |
| #6 (200 mg/l GELRITE, immersed) | 23.3 (12.0) | 36.7 (17.6) | 36.7 (14.5) | 61.8 (9.2) | 39.63 |

TABLE 9

Initiation Frequencies

% of Megagametophytes Initiating - Mean (Standard Error) Genotype

| Treatment | 5-1056 | 21-6 | 5-1036 | H5 | Total |
|---|---|---|---|---|---|
| #1 (no gelling agent) | 0 (0) | 6.7 (6.7) | 13.3 (3.3) | 26.7 (13.3) | 11.7 |
| #2 (100 mg/l GELRITE) | 0 (0) | 30 (11.5) | 6.7 (3.3) | 6.7 (6.7) | 10.9 |
| #3 (200 mg/l GELRITE) | 0 (0) | 13.3 (3.3) | 3.3 (3.3) | 33.3 (8.8) | 12.5 |
| #4 (300 mg/l GELRITE) | 0 (0) | 23.3 (8.8) | 6.7 (3.3) | 30 (15.3) | 15.0 |
| #5 (400 mg/l GELRITE) | 0 (0) | 10 (5.8) | 3.3 (3.3) | 13.3 (3.3) | 6.7 |
| #6 (200 mg/l GELRITE, immersed) | 0 (0) | 13.3 (13.3) | 16.7 (12.0) | 44.1 (11.3) | 18.5 |

Example 4

Use of Brassinolide to Increase Embryogenic Culture Initiation in Loblolly Pine

This experiment measured the effects of varying concentrations of brassinolide on extrusion and initiation in Loblolly pine. The explants in this experiment were megagametophytes isolated from cone collections from four open-pollinated trees, representing a multiplicity of genotypes. The seeds contained Stage 2–4 zygotic embryos. Seeds were sterilized as described in Example 1. Seed coats were split and the megagametophytes were isolated by removing integuments and nucellus. Isolated megagametophytes were placed on solid media. The control treatment was solid media #945 (Table 47) which does not contain brassinolide. The treatment media consisted of media #945 with added brassinolide varying from 0.005 to 0.1 $\mu$M (Table 10). The experiment consisted of three replications per treatment, per genotype. Replications consisted of ten explants in adjacent wells on a single culture well plate. Plates were wrapped in PARAFILM and incubated in the dark at 22–24° C.

After eight weeks, extrusion and initiation were scored as described in Example 3. Extrusion frequency was greater than 50% in all treatments and did not appear to be strongly affected by brassinolide (Table 11). Initiation frequency was increased by the addition of brassinolide at all concentrations (Table 12). There was no clear concentration effect within the tested range. The results demonstrate that brassinolide has a potent effect on initiation even at concentrations as low as 0.005 $\mu$M. Conversely, higher concentrations of brassinolide do not appear to have a detrimental effect upon initiation. One of skill in the art could empirically determine the upper and lower effective concentration of brassinolide which is effective in promoting initiation.

TABLE 10

Treatment Media Compositions

| Treatment # | Media Composition |
|---|---|
| 1 | Basal Media (#945) |
| 2 | Media #992, composed of Basal Media #945 + 0.005 $\mu$M brassinolide |
| 3 | Media #993, composed of Basal Media #945 + 0.01 $\mu$M brassinolide |
| 4 | Media #994, composed of Basal Media #945 + 0.025 $\mu$M brassinolide |
| 5 | Media #995, composed of Basal Media #945 + 0.05 $\mu$M brassinolide |
| 6 | Media #996, composed of Basal Media #945 + 0.1 $\mu$M brassinolide |

TABLE 11

Extrusion by Megagametophytes Cultured in Varying Amounts of Brassinolide

% of Megagametophytes Extruding -Mean (standard error) Genotype

| Treatment | FT | FW | FC | FX | total |
|---|---|---|---|---|---|
| #1 (no Br) | 93.3 (3.3) | 73.3 (8.8) | 27.0 (8.5) | 50.0 (5.8) | 60.9 |
| #2 (0.005 $\mu$M Br) | 96.7 (3.3) | 83.3 (8.8) | 40.0 (5.8) | 53.3 (8.8) | 68.3 |

TABLE 11-continued

Extrusion by Megagametophytes Cultured in
Varying Amounts of Brassinolide

% of Megagametophytes Extruding -Mean (standard error) Genotype

| Treatment | FT | FW | FC | FX | total |
|---|---|---|---|---|---|
| #3 (0.01 μM Br) | 86.7 (8.8) | 50.0 (10.0) | 20.0 (5.8) | 63.3 (14.5) | 55.0 |
| #4 (0.025 μM Br) | 93.3 (6.7) | 64.8 (13.4) | 40.0 (5.8) | 70.0 (5.8) | 67.0 |
| #5 (0.05 μM Br) | 93.3 (3.3) | 70.0 (11.5) | 26.7 (3.3) | 73.3 (8.8) | 65.8 |
| #6 (0.1 μM Br) | 86.7 (3.3) | 73.3 (8.8) | 31.8 (16.5) | 76.7 (8.8) | 67.1 |

Br = brassinolide

TABLE 12

Embryogenic Culture Initiation by Megagametophytes Cultured
in Varying Amounts of Brassinolide % of Megagametophytes Initiating -Mean (standard error) Genotype

| Treatment | FT | FW | FC | FX | total |
|---|---|---|---|---|---|
| #1 (no Br) | 33.3 (3.3) | 16.7 (3.3) | 6.7 (6.7) | 3.3 (3.3) | 15.0 |
| #2 (0.005 μM Br) | 53.3 (12.0) | 20 (5.8) | 0 (0) | 26.7 (8.8) | 25.0 |
| #3 (0.01 μM Br) | 43.3 (16.7) | 3.3 (3.3) | 6.7 (3.3) | 33.3 (12.0) | 21.7 |
| #4 (0.025 μM Br) | 46.7 (12.0) | 20.7 (11.6) | 0 (0) | 23.3 (3.3) | 22.7 |
| #5 (0.05 μM Br) | 53.3 (8.8) | 13.3 (8.8) | 0 (0) | 43.3 (6.7) | 27.5 |
| #6 (0.1 μM Br) | 50 (3.3) | 30 (5.8) | 3.7 (3.7) | 36.7 (8.8) | 30.1 |

Br = brassinolide

Example 5

The Use of Brassinolide to Increase Extrusion and Initiation in Loblolly Pine The promotion of extrusion and initiation in Example 4 was obtained on media containing both brassinolide and abscisic acid (ABA). ABA is known in the art to enhance initiation. This experiment was conducted to determine if brassinolide will promote initiation independently of ABA. The explants were megagametophytes from summer cone collections from four individual trees, each representing a distinct genotype. The seeds contained Stage 2–4 zygotic embryos. Megagametophytes were excised from sterilized seeds, as described in Example 4.

The control media was solid media #1042, which contains no ABA or brassinolide (Table 47). Treatment media were composed of #1042 plus 0, 0.025, 0.10 or 0.25 μM brassinolide (Table 13). While still liquid, 2 ml media was poured into wells on a culture well plate and allowed to solidify. The experiment consisted of three replications per treatment per cone collection. Each replication consisted of ten megagametophytes in adjacent wells on a single well plate. Plates were wrapped with PARAFILM and incubated at 23–24° C. in the dark.

After eight weeks, extrusion and initiation were scored, as described in Example 3. Both extrusion (Table 14) and initiation (Table 15) frequencies were higher in the brassinolide treatments than in the control. There was no clear brassinolide concentration effect within the tested range. These results demonstrate that brassinolide can promote extrusion and initiation, and that the brassinolide enhancement occurs in the absence of ABA. As in Example 4, the lack of a brassinolide concentration effect suggests that lower concentrations (below 0.025 μM) are effective and that higher concentrations (>0.25 μM) are not detrimental. One of skill in the art can empirically determine the optimal effective upper and lower brassinolide concentration limits for solid media.

TABLE 13

Treatment Media Compositions

| Treatment # | Media Composition |
|---|---|
| 1 | Basal Media (#1042) |
| 2 | Media #1043 (Basal Media #1042 + 0.025 μM brassinolide) |
| 3 | Media #1053 (Basal Media #1042 + 0.10 μM brassinolide) |
| 4 | Media #1054 (Basal Media #1042 + 0.25 μM brassinolide) |

TABLE 14

Extrusion by Megagametophytes Cultured in
Varying Amounts of Brassinolide

% of Megagametophytes Extruding -Mean (standard error) Genotype

| Treatment | 11-1055 | 5-1207 | 7-1051 | 11-1507 | total |
|---|---|---|---|---|---|
| #1 (no Br) | 66.7 (12.0) | 13.3 (8.8) | 30.0 (11.5) | 40.0 (5.8) | 37.5 |
| #2 (0.025 μM Br) | 66.7 (3.3) | 38.3 (15.9) | 43.3 (8.8) | 26.7 (6.7) | 43.8 |

TABLE 14-continued

Extrusion by Megagametophytes Cultured in
Varying Amounts of Brassinolide

% of Megagametophytes Extruding -Mean (standard error) Genotype

| Treatment | 11-1055 | 5-1207 | 7-1051 | 11-1507 | total |
|---|---|---|---|---|---|
| #3 (0.10 µM Br) | 63.3 (13.3) | 30.0 (13.3) | 46.7 (13.3) | 36.7 (3.3) | 44.2 |
| #4 (0.25 µM Br) | 70.0 (11.5) | 20.0 (10.0) | 53.3 (12.0) | 23.3 (3.3) | 41.7 |

TABLE 15

Embryogenic Culture Initiation by Megagametophytes Cultured
in Varying Amounts of Brassinolide % of Megagametophytes Initiating -Mean (standard error) Genotype

| Treatment | 11-1055 | 5-1207 | 7-1051 | 11-1507 | total |
|---|---|---|---|---|---|
| #1 (no Br) | 26.7 (12.0) | 10 (10.0) | 10 (5.8) | 30 (5.8) | 19.2 |
| #2 (0.025 µM Br) | 53.3 (6.7) | 27.5 (16.3) | 20 (20.0) | 13.3 (3.3) | 28.5 |
| #3 (0.10 µM Br) | 46.7 (14.5) | 20 (15.3) | 26.7 (8.8) | 16.7 (8.8) | 27.5 |
| #4 (0.25 µM Br) | 53.3 (8.8) | 16.7 (8.8) | 16.7 (8.8) | 13.3 (3.3) | 25.0 |

Example 6

Brassinolide Increases Loblolly Pine Initiation In Liquid Media

In Examples 4 and 5, the effect of varying brassinolide concentration in a solid media was measured. This experiment was conducted to determine the optimal concentration of brassinolide in a liquid media. The explants in this experiment were megagametophytes isolated from the cones of four open-pollinated trees representing a multiplicity of genotypes. The seeds contained Stage 2–4 zygotic embryos. Seeds were sterilized as described in Example 1. Seed coats were split and the megagametophytes were isolated by removing integuments and nucellus. Isolated megagametophytes were wholly immersed in liquid media #1071 (Table 47) containing varying concentrations of brassinolide. The five treatments consisted of media containing zero, 0.05, 0.1, 0.15 and 0.2 µM brassinolide (Table 16). Two ml of each media was poured into wells on culture well plates. Solid media were allowed to solidify. The experiment consisted of four replications per treatment, per cone collection. Replications consisted of ten explants in adjacent wells on a single well plate. Plates were wrapped in PARAFILM and incubated in the dark at 23–24° C.

After eight weeks, extrusion and initiation were scored as described in Example 3. Extrusion and initiation frequencies were very low in cones collected from tree FZ, and megagametophytes from genotype FO did not extrude or initiate any cultures, thus the low frequencies obtained using these two distinct cone collections greatly reduced the overall treatment averages to below 20% for both extrusion and initiation. Nevertheless, overall extrusion frequency was increased in the brassinolide treatments as compared to the control (Table 17). Initiation frequency was increased by the addition of brassinolide from 0.05 to 0.2 µM (Table 18). Because the highest frequency was observed in the 0.2 µM treatment, it is likely that the brassinolide effect was not saturated within the tested range. Nevertheless, one of skill in the art could empirically determine the upper and lower effective concentration of brassinolide which is effective in promoting initiation in a liquid media.

TABLE 16

Treatment Media Compositions

| Treatment # | Media Composition |
|---|---|
| 1 | Basal Media #1071 |
| 2 | Media #1071 + 0.05 µM brassinolide |
| 3 | Media #1071 + 0.1 µM brassinolide |
| 4 | Media #1071 + 0.15 µM brassinolide |
| 5 | Media #1071 + 0.2 µM brassinolide |

TABLE 17

Extrusion by Megagametophytes Cultured in
Varying Amounts of Brassinolide

% of Megagametophytes Extruding -Mean (standard error) Genotype

| Treatment | FN | FX | FO | FZ | total |
|---|---|---|---|---|---|
| #1 (no Br) | 25.0 (8.7) | 12.5 (9.5) | 0.0 (0) | 2.5 (2.5) | 10.0 |
| #2 (0.05 µM Br) | 32.5 (12.5) | 17.5 (6.3) | 0.0 (0) | 0.0 (0) | 12.5 |
| #3 (0.10 µM Br) | 15.0 (6.5) | 27.5 (12.5) | 0.0 (0) | 2.5 (2.5) | 11.3 |

TABLE 17-continued

Extrusion by Megagametophytes Cultured in
Varying Amounts of Brassinolide

% of Megagametophytes Extruding -Mean (standard error) Genotype

| Treatment | FN | FX | FO | FZ | total |
|---|---|---|---|---|---|
| #4 (0.15 μM Br) | 40.0 (20.4) | 15.0 (5.0) | 0.0 (0) | 2.5 (2.5) | 14.4 |
| #5 (0.2 μM Br) | 50.0 (18.3) | 17.5 (4.8) | 0.0 (0) | 0.0 (0) | 16.9 |

Br = brassinolide

TABLE 18

Embryogenic Culture Initiation by Megagametophytes Cultured
in Varying Amounts of Brassinolide % of Megagametophytes Initiating -Mean (standard error) Genotype

| Treatment | FN | FX | FO | FZ | total |
|---|---|---|---|---|---|
| #1 (no Br) | 5.0 (2.9) | 5.0 (5.0) | 0 (0) | 2.5 (2.5) | 3.1 |
| #2 (0.05 μM Br) | 20.0 (10.8) | 17.5 (6.3) | 0 (0) | 0 (0) | 9.4 |
| #3 (0.10 μM Br) | 10.0 (4.1) | 25.0 (10.4) | 0 (0) | 2.5 (2.5) | 9.4 |
| #4 (0.15 μM Br) | 20.0 (12.2) | 12.5 (4.8) | 0 (0) | 2.5 (2.5) | 8.8 |
| #5 (0.2 μM Br) | 35.0 (15.0) | 17.5 (4.8) | 0 (0) | 0 (0) | 13.1 |

Br = brassinolide

Example 7

Vacuum Infiltration of Abscisic Acid Solutions into
Loblolly Pine Megagametophytes In this experiment the effects of megagametophyte pretreatment by vacuum infiltration with abscisic acid solutions of varying concentration was investigated. The explants were megagametophytes from summer cones of four open pollinated individual trees, representing multiplicity of genotypes. The seeds contained Stage 2–4 zygotic embryos. Megagametophytes were excised from sterilized seeds, as described in Example 4.

Prior to culturing, the megagametophytes were vacuum infiltrated with liquid growth media #1036 (see Table 47) containing 0, 1, 5, or 25 ppm abscisic acid (See Table 19 for treatment media compositions). After vacuum infiltration, each megagametophyte was placed on 2 ml solid culture media #1042 (see Table 47 for composition) in a single well on a culture well plate. The experiment consisted of three replications per treatment, per cone collection. Replications consisted of ten explants in adjacent wells on a single well plate. Plates were wrapped in PARAFILM and incubated in the dark at 23–24° C.

After eight weeks, extrusion and initiation were scored, as described in Example 3. Extrusion frequency data is summarized in Table 20 and initiation frequencies are summarized in Table 21. Vacuum infiltration with abscisic acid solution did not promote extrusion or initiation. One possible explanation for the results is that vacuum treatment may damage the megagametophytes. This outcome suggested that alternative means of abscisic acid pre-treatment, such as soaking, should be investigated.

TABLE 19

Abscisic Acid Pre-Treatment Solution Compositions

| Treatment # | Pre-culturing soaking solution |
|---|---|
| 1 | Solution #1036 + 0 ppm abscisic acid |
| 2 | Solution #1036 + 1 ppm abscisic acid |
| 3 | Solution #1036 + 5 ppm abscisic acid |
| 4 | Solution #1036 + 25 ppm abscisic acid |

TABLE 20

Extrusion by Megagametophytes Vacuum Infiltrated with
Varying Amounts of Abscisic Acid
% of Megagametophytes Extruding-Mean
(standard error) Genotype

| Treatment | 11-1055 | 5-1207 | 7-1051 | 11-1507 | total |
|---|---|---|---|---|---|
| 1 | 75.5 (4.5) | 16.7 (3.3) | 33.3 (6.7) | 13.3 (8.8) | 34.7 |
| 2 | 53.3 (3.3) | 23.3 (14.5) | 33.3 (8.8) | 16.7 (6.7) | 31.7 |
| 3 | 66.7 (12.0) | 10.0 (5.8) | 30.0 (11.5) | 6.7 (3.3) | 28.4 |
| 4 | 36.7 (3.3) | 13.3 (13.3) | 56.7 (12.0) | 6.7 (3.3) | 28.4 |

TABLE 21

Embryogenic Culture Initiation by Megagametophytes Vacuum
Infiltrated with Varying Amounts of Abscisic Acid
% of Megagametophytes Initiating-Mean
(standard error) Genotype

| Treatment | 11-1055 | 5-1207 | 7-1051 | 11-1507 | total |
|---|---|---|---|---|---|
| 1 | 20.4 (5.5) | 6.7 (3.3) | 16.7 (8.8) | 10 (5.8) | 13.5 |
| 2 | 16.7 (3.3) | 20 (11.5) | 6.7 (3.3) | 6.7 (6.7) | 12.5 |
| 3 | 30 (11.5) | 10 (5.8) | 10 (5.8) | 6.7 (3.3) | 14.2 |
| 4 | 13.3 (3.3) | 10 (10.0) | 13.3 (8.8) | 0 (0.0) | 9.2 |

Example 8

The Effects of Abscisic Acid Soaking Pre-treatment and Brassinolide on Extrusion and Initiation in Loblolly Pine In this experiment, the effects of ovule pre-treatment by soaking with abscisic acid solutions of varying concentration was investigated. The abscisic acid treatment was tested on two media, one containing brassinolide and one lacking in brassinolide. The explants were megagametophytes from open pollinated summer cones of four individual trees, representing a multiplicity of genotypes. The seeds contained Stage 2–4 zygotic embryos. Megagametophytes were excised from sterilized seeds, as described in Example 4.

Treatments are summarized in Table 22. Prior to culturing, the megagametophytes were soaked for 30 minutes in liquid growth media (media #1042, Table 47, minus the gelling agent) containing 0, 5, 10 and 20 ppm abscisic acid. After soaking, the megagametophytes were placed on either one of two solid growth media. While still liquid, 2 ml media was poured into wells on a culture well plate and allowed to solidify. Half the soaked megagametophytes were placed on solid media #1042 (Table 47) and half were placed on solid media #1042 with 0.1 $\mu$M brassinolide added. The solid media on which the megagametophytes were cultured did not contain ABA. The experiment consisted of three replications per treatment, per cone collection. Replications consisted of ten explants in adjacent wells on a single well plate. Plates were wrapped in PARAFILM and incubated in the dark at 23–24° C.

After eight weeks, extrusion and initiation were scored, as described in Example 3. Extrusion frequency data is summarized in Table 23 and initiation frequencies are summarized in Table 24. On media where no brassinolide was present (Treatments #1–4) the abscisic acid pretreatment did not promote extrusion or initiation. On solid media where brassinolide was present, there was a dramatic difference in extrusion and initiation between megagametophytes soaked in zero and 5 ppm ABA solutions (Treatments #5 and #6) compared to those soaked in 10 and 20 ppm ABA solutions (Treatments #7 and #8). Megagametophytes in treatment #5 did not extrude at all an consequently, had zero culture initiations. Likewise, megagametophytes in treatment #6 had a very low frequency of extrusion and consequently initiated few cultures. In contrast, megagametophytes treated with higher amounts of ABA in Treatments 7 and 8 had the highest initiation frequencies of any treatment. The extremely low frequencies observed in Treatments #5 and #6 suggest that some kind of experimental error occurred. Alternatively, there may have been an interaction between brassinolide and ABA such that low ABA plus brassinolide inhibits extrusion, with this inhibition overcome when ABA concentration is higher. Overall, the results suggest that pre-treatment with higher concentrations of ABA in combination with brassinosteroid-containing media can enhance extrusion and initiation.

TABLE 22

Pre-Treatment Solution and Culture Media Treatments

| | ABA Soaking Solution | Culture Media |
| --- | --- | --- |
| Treatment #1 | Liquid #1042 (#1042 minus gelling agent) | #1042 (See Table 13) |
| Treatment #2 | Liquid #1042 + 5 ppm ABA | #1042 |
| Treatment #3 | Liquid #1042 + 10 ppm ABA | #1042 |
| Treatment #4 | Liquid #1042 + 20 ppm ABA | #1042 |
| Treatment #5 | Liquid #1042 | #1042 + 0.10 $\mu$M brassinolide |
| Treatment #6 | Liquid #1042 + 5 ppm ABA | #1042 + 0.10 $\mu$M brassinolide |
| Treatment #7 | Liquid #1042 + 10 ppm ABA | #1042 + 0.10 $\mu$M brassinolide |
| Treatment #8 | Liquid #1042 + 20 ppm ABA | #1042 + 0.10 $\mu$M brassinolide |

TABLE 23

Extrusion by Megagametophytes Pre-Treated With Varying Amounts of Abscisic Acid On Media With or Without Brassinolide % Megagametophytes Extruding - Mean (standard error) Genotype

| Treatment | 7-1051 | TC11-109 | TC5-1501 | M7-56 | total |
| --- | --- | --- | --- | --- | --- |
| #1-0 ppm ABA/No Br | 46.7 (8.8) | 30.0 (5.8) | 60.0 (5.8) | 10.0 (0.0) | 36.7 |
| #2-5 ppm ABA/No Br | 53.3 (8.8) | 33.3 (3.3) | 33.3 (6.7) | 20.0 (5.8) | 35.0 |
| #3-10 ppm ABA/No Br | 30.0 (5.8) | 46.7 (13.3) | 16.7 (8.8) | 26.7 (6.7) | 30.0 |
| #4-20 ppm ABA/No Br | 40.0 (5.8) | 46.7 (12.0) | 40.0 (11.5) | 36.7 (8.8) | 40.9 |
| #5-0 ppm ABA/ +Br | 13.3 (6.7) | 0.0 (0.0) | 0.0 (0.0) | 3.3 (3.3) | 4.2 |
| #6-5 ppm ABA/ +Br | 6.7 (3.3) | 0.0 (0.0) | 6.7 (3.3) | 0.0 (0.0) | 3.4 |
| #7-10 ppm ABA/ +Br | 33.3 (3.3) | 63.3 (12.0) | 50.0 (5.8) | 43.3 (14.5) | 47.5 |
| #8-20 ppm ABA/ +Br | 53.3 (3.3) | 40.0 (5.8) | 50.0 (10.0) | 36.7 (6.7) | 45.0 |

Br = brassinolide

TABLE 24

Embryogenic Culture Initiation by Megagametophytes Pre-Treated
With Varying Amounts of Abscisic Acid On Media With or Without Brassinolide
% Megagametophytes Extruding - Mean
(standard error) Genotype

| Treatment | 7-1051 | TC11-109 | TC5-1501 | M7-56 | total |
|---|---|---|---|---|---|
| #1-0 ppm ABA/No Br | 26.7 (13.3) | 6.7 (3.3) | 16.7 (6.7) | 6.7 (3.3) | 14.2 |
| #2-5 ppm ABA/No Br | 20.0 (10.0) | 10.0 (5.8) | 10.0 (0.0) | 13.3 (3.3) | 13.3 |
| #3-10 ppm ABA/No Br | 6.7 (3.3) | 13.3 (3.3) | 3.3 (3.3) | 13.3 (3.3) | 9.2 |
| #4-20 ppm ABA/No Br | 13.3 (3.3) | 13.3 (3.3) | 6.7 (3.3) | 6.7 (6.7) | 10.0 |
| #5-0 ppm ABA/ +Br | 0.0 (0.0) | 0.0 (0.0) | 0.0 (0.0) | 0.0 (0.0) | 0 |
| #6-5 ppm ABA/ +Br | 3.3 (3.3) | 0.0 (0.0) | 0.0 (0.0) | 0.0 (0.0) | 0.8 |
| #7-10 ppm ABA/ +Br | 20.0 (5.8) | 26.7 (14.5) | 23.3 (3.3) | 10.0 (5.8) | 20 |
| #8-20 ppm ABA/ +Br | 23.3 (3.3) | 16.7 (3.3) | 16.7 (8.8) | 13.3 (3.3) | 17.5 |

Br = brassinolide

Example 9

Elevated Pressure Increases Extrusion and Initiation in Loblolly Pine

This experiment demonstrates the enhancing effects of elevated atmospheric pressure on embryogenic culture initiation. Additionally, this experiment tested the effects of excluding plant growth regulators from the culture media. Loblolly pine megagametophytes were excised from summer cones of three individual open pollinated trees, representing a multiplicity of genotypes. The seeds contained Stage 2–4 zygotic embryos. Megagametophytes were excised from sterilized seeds, as described in Example 4 and placed on one of two solid media treatments. Solid media #716 contained silver nitrate, ABA, auxin and cytokinin (Table 47). Solid media #897 contained no silver nitrate, ABA, auxin or cytokinin. The experiment consisted of three replications per treatment, per cone collection. Replications consisted of ten explants in adjacent wells on a single well plate. Plates were wrapped in PARAFILM and incubated in the dark at 23–24° C.

In the elevated atmospheric pressure treatments, the culture plates were placed in a pressure vessel constructed from a benchtop autoclave. The top of the pressure chamber was sealed with a rubber tubing gasket and modified to include an inlet valve. A pressure of 1.5 atmospheres was applied throughout the culture period using a tank of compressed air.

After eight weeks, extrusion and initiation were scored, as described in Example 3. Extrusion frequency data is summarized in Table 25. Initiation treatment data is summarized in Table 26. Megagametophytes cultured on media #716 under elevated pressure extruded tissue and initiated embryogenic cultures at a higher frequency than megagametophytes cultured at atmospheric pressure. Elevated pressure increased extrusion by almost 50% and doubled the frequency of initiation. On media #897, extrusion and initiation were greatly reduced compared to the #716 treatment. Elevated pressure enhanced initiation on #897 as it did on media #716. Thus, the results illustrate the strong positive effect of elevated pressure on extrusion and initiation. The superior performance of media #716 demonstrates the importance of growth regulators in enhancing the initiation of embryogenic cultures.

TABLE 25

Extrusion Frequency
% Megagametophytes Extruding - Mean
(standard error) Genotype

| Treatment | FO | FX | FU | total |
|---|---|---|---|---|
| #716 | 25.83 (5.8) | 20.0 (5.8) | 48.33 (13.3) | 31.39 |
| #716 + Pressure | 42.60 (7.3) | 40.73 (9.3) | 60.00 (5.8) | 47.78 |
| #897 | 17.77 (9.7) | 23.33 (6.7) | 16.67 (8.8) | 19.26 |
| #897 + Pressure | 10.33 (5.2) | 28.50 (3.3) | 10.00 (5.8) | 16.28 |

TABLE 26

Initiation Frequency
% Megagametophytes Initiating - Mean
(standard error) Genotype

| Treatment | FO | FX | FU | total |
|---|---|---|---|---|
| 716 | 15.00 (7.6) | 6.70 (3.3) | 23.30 (13.3) | 15.0 |
| 716 + Pressure | 37.90 (2.8) | 23.70 (8.8) | 26.70 (12.0) | 29.4 |
| 897 | 0.00 (0.0) | 6.70 (3.3) | 6.70 (3.3) | 4.5 |
| 897 + Pressure | 6.70 (6.7) | 14.00 (3.0) | 3.30 (3.3) | 8.0 |

Example 10

Elevated Pressure Effect on Extrusion and Initiation on Various Media Compositions in Loblolly Pine The results in Example 9 suggest that extrusion and initiation are negatively affected when culture media constituents such as auxin and cytokinin, as well as silver nitrate and ABA are absent. This experiment tested media containing various different combinations of growth regulating components. Additionally, these media were cultured under normal or elevated atmospheric pressure to determine if pressure interacts with media components.

The megagametophytes were excised from summer cones of three individual open pollinated trees, representing a multiplicity of genotypes. The seeds contained Stage 2–4 zygotic embryos. Megagametophytes were excised from sterilized seeds, as described in Example 4 and placed on various media compositions described in Table 47. Media #889 had a normal composition with all growth regulating compounds present. The other treatment media were based on #889, with specific components excluded. Media #888 contained no cGMP. Media #887 contained no cGMP, AgNO$_3$, or ABA. Media #971 contained no AgNO$_3$, cGMP, ABA or activated charcoal. Media #972 contained no cytokinins. Each media was cultured either at atmospheric pressure or at an elevated pressure of 1.5 atmospheres. The experiment consisted of three replications per treatment, per cone collection. Replications consisted of ten explants in adjacent wells on a single well plate. Plates were wrapped in PARAFILM and incubated in the dark at 23–24° C.

After eight weeks, extrusion and initiation were scored, as described in Example 3. Extrusion frequency data is summarized in Table 27. Initiation treatment data is summarized in Table 28. Elevated pressure slightly increased extrusion and initiation frequency of megagametophytes cultured on complete media #889. Elevated pressure also enhanced extrusion and initiation in the absence of cytokinins (media #972).

As in Example 9, the explants in this experiment were megagametophytes, containing Stage 2–4 somatic embryos, excised from the open pollinated summer cones of four different genotypes of Loblolly pine. Megagametophytes were isolated as in Example 4 and put on initiation media #889 (Table 47). The experiment consisted of three replications per treatment, per cone collection. Replications consisted of ten explants in adjacent wells on a single well plate. Plates were wrapped in PARAFILM and incubated in the dark at 23–24° C.

Explants were cultured on solid media under atmospheres containing three levels of oxygen: normal air (21% oxygen), 30% oxygen and 50% oxygen. All oxygen treatments were applied at either normal atmospheric pressure or under an elevated pressure of 1.5 atmospheres.

After eight weeks, extrusion and initiation were scored, as described in Example 3. Extrusion frequency data is sum-

TABLE 27

Extrusion Frequencies
% Megagametophytes Extruding - Mean
(standard error) Genotype

| Treatment | 11-1055 | 11-1223 | H4 | L4 | Total |
|---|---|---|---|---|---|
| #887 | 63.3 (12.0) | 20 (10.0) | 36.7 (16.7) | 23.3 (3.3) | 35.83 |
| #887 + Pressure | 80 (5.8) | 23.3 (14.5) | 47.0 (27.0) | 6.7 (6.7) | 39.25 |
| #888 | 56.7 (12.0) | 13.3 (3.3) | 40 (20.8) | 30 (5.8) | 35.00 |
| #888 + Pressure | 76.7 (12.0) | 23.7 (8.5) | 26.7 (26.7) | 16.7 (8.8) | 35.95 |
| #889 | 66.7 (6.7) | 33.3 (8.8) | 46.7 (16.7) | 23.3 (8.8) | 42.50 |
| #889 + Pressure | 80 (0.0) | 16.7 (3.3) | 23.3 (23.3) | 20.0 (11.5) | 35.00 |
| #971 | 40.4 (17.0) | 40 (11.5) | 33.3 (20.3) | 3.3 (3.3) | 29.25 |
| #971 + Pressure | 60.7 (3.3) | 36.7 (12.0) | 30 (11.5) | 10.4 (5.8) | 34.45 |
| #972 | 23.3 (8.8) | 16.7 (8.8) | 13.3 (13.3) | 6.7 (6.7) | 15.00 |
| #972 + Pressure | 50 (5.8) | 40 (5.8) | 43.3 (8.8) | 30.0 (5.8) | 40.83 |

TABLE 28

Initiation Frequencies
% Megagametophytes Initiating - Mean
(standard error) Genotype

| Treatment | 11-1055 | 11-1223 | H4 | L4 | Total |
|---|---|---|---|---|---|
| 887 | 23.3 (8.8) | 0 (0) | 20 (0.0) | 23.3 (8.8) | 16.7 |
| 887 + Pressure | 13.3 (3.3) | 3.3 (3.3) | 35.9 (16.3) | 6.7 (6.7) | 14.8 |
| 888 | 0 (0) | 3.3 (3.3) | 26.7 (8.8) | 30 (30) | 15.0 |
| 888 + Pressure | 0 (0) | 6.7 (3.3) | 3.3 (3.3) | 16.7 (8.8) | 6.7 |
| 889 | 16.7 (6.7) | 0 (0) | 36.7 (6.7) | 23.3 (8.8) | 19.2 |
| 889 + Pressure | 23.3 (8.8) | 13.3 (3.3) | 23.3 (8.8) | 30 (5.8) | 22.5 |
| 971 | 10.4 (5.8) | 10 (10.0) | 23.3 (12.0) | 3.3 (3.3) | 11.8 |
| 971 + Pressure | 10 (5.8) | 6.7 (3.3) | 13.3 (8.8) | 10.4 (5.8) | 10.1 |
| 972 | 0 (0) | 0 (0) | 0 (0) | 6.7 (6.7) | 1.7 |
| 972 + Pressure | 0 (0) | 0 (0) | 0 (0) | 20 (11.5) | 5.0 |

Example 11

Effects of Elevated Pressure and Increased Oxygen on Extrusion and Initiation in Loblolly Pine The experiment in Example 9 demonstrates that elevated atmospheric pressure can increase extrusion and initiation rates. This experiment was conducted to test whether the pressure effect observed in Experiment 9 was due to the pressure itself or the increased oxygen partial pressure that explants would experience at elevated atmospheric pressure.

marized in Table 29. Initiation treatment data is summarized in Table 30. Elevated pressure increased extrusion and initiation in the normal 21% oxygen treatment and in the 30% oxygen treatment. In the 50% oxygen treatment, elevated pressure actually reduced initiation. The results suggest that the elevated pressure effect in Example 8 was not due to the increased partial pressure of oxygen and may instead be the effect of increased hydrostatic forces. Increased oxygen generally decreased extrusion and initiation in both pressure treatments.

TABLE 29

Extrusion Frequencies
% Megagametophytes Extruding - Mean
(standard error) Genotype

| Treatment | 11-1057 | 18-120 | 5-1036 | 18-1212 | Total |
|---|---|---|---|---|---|
| air (21% Oxygen) | 33.3 (3.3) | 23.3 (12.0) | 50.0 (11.5) | 73.3 (3.3) | 45.0 |
| air + Pressure | 42.1 (4.8) | 70.0 (17.3) | 82.6 (9.0) | 46.3 (6.7) | 60.3 |
| 30% Oxygen | 30.0 (15.3) | 33.3 (19.2) | 57.5 (3.8) | 60.3 (8.0) | 45.3 |
| 30% Oxygen + Pressure | 34.4 (16.1) | 16.7 (8.8) | 73.3 (8.8) | 88.4 (6.5) | 53.2 |
| 50% Oxygen | 53.3 (3.3) | 40.0 (10.0) | 50.0 (10.0) | 56.0 (3.6) | 49.8 |
| 50% Oxygen + Pressure | 43.3 (3.3) | 30.8 (3.6) | 83.3 (3.3) | 70.0 (15.3) | 56.9 |

TABLE 30

Initiation Frequencies
% Megagametophytes Initiating - Mean
(standard error) Genotype

| Treatment | 11-1057 | 18-120 | 5-1036 | 18-1212 | Total |
|---|---|---|---|---|---|
| air (21% Oxygen) | 10.0 (5.8) | 0.0 (0.0) | 16.7 (3.3) | 16.7 (6.7) | 10.9 |
| air + Pressure | 9.7 (5.0) | 25.0 (2.9) | 10.4 (5.8) | 7.0 (3.5) | 13.0 |
| 30% Oxygen | 10.0 (0.0) | 0.0 (0.0) | 3.3 (3.3) | 10.4 (5.8) | 5.9 |
| 30% Oxygen + Pressure | 6.7 (67) | 6.7 (6.7) | 13.3 (3.3) | 3.7 (3.7) | 7.6 |
| 50% Oxygen | 13.0 (3.3) | 0.0 (0.0) | 20.0 (5.8) | 11.2 (0.7) | 11.1 |
| 50% Oxygen + Pressure | 10.0 (5.8) | 4.2 (4.2) | 13.3 (3.3) | 10.0 (5.8) | 8.6 |

Example 12

Optimization of Atmospheric Pressure to Enhance Extrusion and Initiation in Loblolly Pine This experiment was performed to determine the optimal atmospheric pressure for promoting somatic embryogenesis. The explants in this experiment were megagametophytes, containing Stage 2–4 somatic embryos, excised from the open pollinated summer cones of four different genotypes of Loblolly pine. Megagametophytes were isolated as in Example 4 and put on initiation media #889 (Table 47). The experiment consisted of three replications per treatment, per cone collection. Replications consisted of ten explants in adjacent wells on a single well plate. Plates were wrapped in PARAFILM and incubated in the dark at 23–24° C.

The experiment consisted of culturing explants at either normal atmospheric pressure, or an elevated pressure of 1.25, 1.5, 2.0 or 2.5 atmospheres. After eight weeks, extrusion and initiation were scored, as described in Example 3. Extrusion frequency data is summarized in Table 34. Initiation treatment data is summarized in Table 35. Culturing under 1.5 atmospheres gave the highest frequencies of extrusion and initiation (16.5%), suggesting that the optimal pressure for promoting initiation is 1.5 atmospheres.

TABLE 31

Extrusion Frequency
% Megagametophytes Extruding - Mean
(standard error) Genotype

| Treatment | 18-1212 | 11-1123 | 7-1051 | N4 | Total |
|---|---|---|---|---|---|
| Normal | 66.7 (6.7) | 20.0 (5.8) | 30.0 (5.8) | 70.0 (11.5) | 46.7 |
| 1.25 atmosphere | 80.0 (5.8) | 40.0 (5.8) | 23.3 (12.0) | 63.3 (3.3) | 51.7 |
| 1.5 atmosphere | 63.3 (12.0) | 43.3 (12.0) | 37.0 (15.5) | 59.7 (5.0) | 50.8 |
| 2 atmosphere | 80.0 (10.0) | 33.3 (6.7) | 40.0 (5.8) | 66.7 (6.7) | 55.0 |
| 2.5 atmosphere | 80.0 (5.8) | 33.3 (3.3) | 33.3 (8.8) | 50.0 (15.3) | 49.2 |

TABLE 32

Initiation Frequency
% Megagametophytes Initiating - Mean
(standard error) Genotype

| Treatment | 18-1212 | 11-1123 | 7-1051 | N4 | Total |
|---|---|---|---|---|---|
| Normal | 20 (5.8) | 0 (0.0) | 6.7 (3.3) | 26.7 (12.0) | 13.4 |
| 1.25 atmosphere | 23.3 (6.7) | 3.3 (3.3) | 0.0 (0.0) | 23.3 (3.3) | 12.5 |
| 1.5 atmosphere | 25.8 (79) | 3.3 (3.3) | 6.7 (6.7) | 30.4 (11.2) | 16.6 |
| 2 atmosphere | 16.7 (8.8) | 10 (5.8) | 0.0 (0.0) | 10.0 (5.8) | 9.2 |
| 2.5 atmosphere | 6.7 (3.3) | 0 (0.0) | 3.3 (3.3) | 10.0 (5.8) | 5.0 |

Example 13

Elevated Pressure Enhancement of Extrusion and Initiation in Combination with Other Methods in Loblolly Pine The previous examples indicate that elevated pressure can enhance extrusion and initiation. This experiment was designed to test the effect of elevated pressure in combination with other treatments to determine the optimal conditions for promoting extrusion and initiation.

The explants in this experiment were megagametophytes, containing Stage 2–4 somatic embryos, excised from the open pollinated summer cones of three different genotypes of Loblolly pine. Megagametophytes were isolated as in Example 4 and put on various treatment media, described in Table 33. Megagametophytes in some treatments received a 30 minute pre-culturing soak in liquid media (#1042 minus the gelling agent) containing 5 ppm ABA. Megagametophytes in Treatments 9 and 10 were fully immersed in liquid media #1038. The experiment consisted of three replications per treatment, per genotype. Replications consisted of ten explants in adjacent wells on a single well plate. Plates were wrapped in PARAFILM and incubated in the dark at 23–24° C.

Five different treatments were used, each cultured under 1.0 or 1.5 atmospheres for a total of ten treatments (See Table 33).

TABLE 33

Treatments

| # | Treatment |
|---|---|
| 1 | Media #1042 |
| 2 | Media #1042 + 1.5 atm pressure |
| 3 | Media #1042 + 0.1 μM brassinolide |
| 4 | #4-#1042 + 0.1 μM brassinolide + 1.5 atm pressure |
| 5 | #5-ABA Pre soak |
| 6 | #6-ABA Pre soak + 1.5 atm pressure |
| 7 | #7-ABA Pre soak + 0.1 μM brassinolide |
| 8 | #8-ABA Pre soak + 0.1 μM brassinolide + 1.5 atm pressure |
| 9 | #9-Liquid Media #1038 |
| 10 | #10-Liquid Media #1038 + 1.5 atm pressure |

After 8 weeks culturing, the treatments were scored. Extrusion frequency data is summarized in Table 34. Initiation treatment data is summarized in Table 35. Extrusion and initiation were increased by elevated pressure in all treatments.

As noted previously, Loblolly pine is a species recalcitrant to somatic embryogenesis. The previous examples demonstrate the generally low frequency of initiation in this species, in the range of 15–25%. Thus, even modest improvements in initiation frequency are valuable. Evaluation of methods is complicated by the genetic variability among individual Loblolly pine trees in their amenability to somatic embryogenesis. Further complicating the picture is the fact that open pollinated trees will have genetically diverse seeds, even within a single cone. Consequently, any particular cone may have a stochastically high (or low) tendency to initiate a culture. Thus, when evaluating a method of improving the initiation of embryogenic cultures, the genetic composition of the seeds used in each experiment can significantly effect the results.

The initiation frequencies in this experiment were generally quite high. For example, on the control media (Treatment #1—solid media containing no ABA) initiation frequency was over 26%, which is high compared to the frequencies obtained using this media in other experiments (for example, 14.2% in Example 8). The differences observed between experiments illustrates the genetic variability in amenability to somatic embryogenesis that is present in Loblolly pine. The effect of genetic background on initiation is even more striking when one compares results among the different genotypes within each experiment.

In the treatments applied at normal pressure, ABA and brassinolide did not enhance extrusion or initiation (compare Treatment #1 with #3, #5 and #7). The high frequencies observed across the solid media treatments in this experiment, compared to other experiments, suggest that the seeds from these particular cones were somewhat more amenable to somatic embryogenesis. As noted above, initiation frequencies in this experiment were relatively high, suggesting that due to inherent genetic factors, these seeds had a high potential for initiation at normal pressure. Consistent with this, positive effects of brassinolide and ABA were not observed in these genotypes. Thus, it is possible that the effects of brassinolide and ABA treatments were masked by the high innate potential of these seeds for embryogenic culture initiation. Had more recalcitrant varieties been used, the influence of these factors may have been more apparent.

In contrast, pressure had strong effects in all treatments, especially when ABA and brassinolide treatments were also applied. In the treatments cultured under elevated pressure, the influence of brassinolide and ABA was clearly visible. Initiation frequency in the control treatment was enhanced by only 8.8% under elevated pressure (Treatment #2 vs. #1). In contrast, in the presence of brassinolide, pressure increased initiation frequency by over 60% (Treatment #4 vs. #3). When elevated pressure was applied to explants treated with a combination of brassinolide and ABA, initiation frequency was increased by 83% (Treatment #8 vs. #7).

These results demonstrate the effectiveness of ABA and brassinolide in enhancing the elevated pressure effect. Treatments #4 and #8 had the higher initiation frequencies than those observed in most of the Examples. These high rates over 35% are within the range of effectiveness needed for commercial application. Further, the consistent pressure effect across all treatments, including the liquid media treatment, demonstrates the broad applicability of using elevated pressure to increase initiation.

TABLE 34

Extrusion Frequencies
% Megagametophytes Extruding - Mean
(standard error) Genotype

| Treatment | 21-6 | 7-100 | 11-1095 | Total |
|---|---|---|---|---|
| #1- media #1042 | 73.3 (8.0) | 6.7 (3.3) | 33.3 (12.0) | 37.8 |
| #2- + Pressure | 60.0 (5.0) | 17.5 (6.3) | 49.0 (5.0) | 42.2 |
| #3- + Br | 36.7 (6.7) | 3.3 (3.3) | 56.7 (6.7) | 32.2 |
| #4- Br + Pressure | 74.4 (12.4) | 43.3 (8.8) | 50.0 (21.7) | 55.9 |
| #5- ABA soak | 55.2 (8.7) | 10.0 (5.8) | 50.0 (0.0) | 38.4 |
| #6- ABA soak + Pressure | 66.7 (8.8) | 23.3 (13.3) | 50.0 (5.8) | 46.7 |
| #7- ABA soak + Br | 50.0 (0.0) | 26.7 (8.8) | 26.7 (3.3) | 34.5 |
| #8- ABA soak + Br + Pressure | 70.0 (5.8) | 36.2 (3.8) | 70.0 (5.8) | 58.7 |
| #9- Liquid Media (#1038) | 26.7 (13.3) | 0.0 (0.0) | 6.7 (3.3) | 11.1 |
| #10- Liquid Media + Pressure | 59.2 (10.9) | 0.0 (0.0) | 30.0 (5.8) | 29.7 |

TABLE 35

Initiation Frequencies
% Megagametophytes Initiating - Mean
(standard error) Genotype

| Treatment | 21-6 | 7-100 | 11-1095 | Total |
|---|---|---|---|---|
| #1- media #1042 | 56.7 (6.7) | 3.3 (3.3) | 20.0 (5.8) | 26.7 |
| #2- + Pressure | 47.6 (2.4) | 3.3 (3.3) | 36.2 (3.8) | 29.0 |
| #3- + Br | 33.3 (8.8) | 0.0 (0.0) | 39.2 (11.6) | 24.2 |
| #4- Br + Pressure | 56.9 (13.7) | 20.0 (5.8) | 39.2 (18.6) | 38.7 |
| #5- ABA soak | 37.8 (11.8) | 3.3 (3.3) | 23.3 (6.7) | 21.5 |
| #6- ABA soak + Pressure | 50.0 (11.5) | 3.3 (3.3) | 20.0 (5.8) | 24.4 |
| #7- ABA soak + Br | 40.0 (5.8) | 3.3 (3.3) | 16.7 (8.8) | 20.0 |
| #8- ABA soak + Br + Pressure | 46.7 (6.7) | 10.0 (5.8) | 53.3 (8.8) | 36.7 |
| #9- Liquid Media (#1038) | 6.7 (6.7) | 0.0 (0.0) | 3.3 (3.3) | 3.3 |
| #10- Liquid Media + Pressure | 29.8 (7.4) | 0.0 (0.0) | 3.3 (3.3) | 11.0 |

Example 14

High Rates of Loblolly Pine Initiation Using a
Solid-Liquid Media Combination

This Example demonstrates a novel method of initiating embryogenic cultures using a combination of solid and liquid media. Although extrusion frequencies on solid media are generally high, the use of liquid media is very desirable because of the amenability of liquid media techniques to automation. Moreover, the use of liquid media facilitates culture transfers and therefore saves valuable time and labor. Therefore it was our objective to develop a two-step system in which megagametophytes would extrude on a solid media before being immersed in a liquid initiation media. This experiment demonstrates the efficacy of such a system. Additionally, the experiment tested the effects of media changes and explant transfers on extrusion and initiation.

Megagametophyte explants were isolated from the cones of four open-pollinated trees representing a multiplicity of genotypes. The seeds contained Stage 2–4 zygotic embryos. Seeds were sterilized as described in Example 1. Seed coats were split and the megagametophytes were isolated by removing integuments and nucellus. Isolated megagametophytes were cultured under one of six treatments (Table 36).

Treatment #1 consisted of each megagametophyte being immersed in 2 ml liquid media in a culture well on a culture well plate. The liquid media was #1081 (Table 47) containing 0.1 µM brassinolide. In Treatment #2 megagametophytes were immersed in liquid media, as in Treatment #1, and then 1 ml of fresh liquid media was added to the well after four weeks to test the effects of adding fresh media.

Treatment #3 consisted of culturing megagametophytes on 2 ml of solid media #1042 (Table 47) for eight weeks.

Treatment #4 consisted of culturing explants on solid media, as in Treatment #3, and after four weeks, carefully transferring the megametophyte and any extruded tissues to fresh solid media. Treatment #3 provides a control treatment for comparison to the two step process. Treatment #4 was performed to determine the effect of physically moving the megagametophytes and the effect of fresh media.

Treatments #5 and #6 tested two embodiments of the two-step system. In Treatment #5, the megagametophytes were placed on solid media #1042 for four weeks and then transferred to a new wells where they were immersed in 2 ml liquid media #1081 for four weeks. In Treatment #6, each megagametophyte was placed on solid media in a single well of a culture well plate. After four weeks, 1 ml liquid media #1081 was poured over the megagametophytes, immersing them.

The experiment consisted of four replications per treatment, per genotype. Replications consisted of ten explants in adjacent wells on a single well plate. Plates were wrapped in PARAFILM and incubated in the dark at 23–24° C.

After four weeks, the secondary treatment was applied to the explants. Preliminary measurements of extrusion were performed at this time. In all treatments the majority of extrusion had occurred by this point. Four weeks later extrusion and initiation were scored as described in Example 3. The final extrusion frequencies after eight weeks are summarized in Table 37. Initiation frequencies after eight weeks are summarized in Table 38.

In the liquid media treatment #2, the addition of fresh liquid media after eight weeks did not enhance extrusion or initiation compared to Treatment #1. Among the four treatments where extrusion took place on solid media (Treatments #3–6) extrusion frequency was around 60%. Initiation was highest (43–44%) in the two-step treatments where megagametophytes were cultured in liquid media after extruding on solid media, compared to Treatments #3 and #4 where megagametophytes were left on solid media (33–37%). These results demonstrate the advantage of using a solid and liquid media two step combination to achieve high rates of initiation. Initiation frequencies were essentially the same in Treatments #5 and 6, suggesting that the physical disruption of the transfer from solid media did not negatively affect initiation. Although Treatments #5 and 6 appear to be equally efficacious in promoting initiation, the method of Treatment #6, where media is simply poured over the megagametophytes, required no time-consuming manipulation of the megagametophytes and is therefore preferred.

TABLE 36

| Treatment # | First Media | Second Treatment at 4 Weeks |
| --- | --- | --- |
| 1 | Liquid Media #1081 | None |
| 2 | Liquid Media #1081 | 1 ml Liquid Media Added |
| 3 | Solid Media #1043 | None |
| 4 | Solid Media #1043 | Explant transferred to fresh solid media #1043 |
| 5 | Solid Media #1043 | Explant transferred to fresh liquid media #1043 |
| 6 | Solid Media #1043 | 1 ml fresh liquid media poured over explant |

TABLE 37

Frequency of Extrusion
% of Megagametophytes Extruding-Mean
(standard error) Genotype

| Treatment | FN | FX | FO | FZ | total |
| --- | --- | --- | --- | --- | --- |
| #1 (liquid) | 22.5 (5) | 57.5 (16.5) | 0 (0) | 0 (0) | 20.0 |
| #2 (liquid + liquid) | 5.0 (5.0) | 50.0 (10.0) | 0 (0) | 2.5 (2.5) | 14.4 |
| #3 (solid) | 74.7 (4.7) | 62.5 (14.4) | 70.5 (13.0) | 40.8 (20.3) | 62.1 |
| #4 (solid to solid) | 67.5 (6.3) | 65.0 (19.4) | 61.1 (9.6) | 40.0 (22.7) | 58.4 |
| #5 (solid to liquid) | 77.5 (4.8) | 72.5 (14.9) | 48.0 (10.1) | 57.5 (25.3) | 63.9 |
| #6 (solid + liquid) | 67.2 (6.3) | 65.0 (15.5) | 58.0 (8.9) | 46.7 (22.6) | 64.2 |

TABLE 38

Embryogenic Culture Initiation
% of Megagametophytes Initiating-Mean
(standard error) Genotype

| Treatment | FN | FX | FO | FZ | total |
| --- | --- | --- | --- | --- | --- |
| #1 (liquid) | 15.0 (9.6) | 45.0 (15.5) | 0 (0) | 0 (0) | 15.0 |
| #2 (liquid + liquid) | 0.0 (0) | 35.0 (9.6) | 0 (0) | 2.5 (2.5) | 9.4 |
| #3 (solid) | 36.1 (5.5) | 27.5 (11.8) | 48.2 (10.1) | 35.8 (22.5) | 36.9 |
| #4 (solid to solid) | 25.0 (2.9) | 40.0 (10.8) | 41.6 (2.8) | 27.5 (13.1) | 33.5 |
| #5 (solid to liquid) | 65.0 (6.5) | 40.0 (9.1) | 42.8 (7.8) | 24.2 (14.7) | 43.0 |
| #6 (solid + liquid) | 66.4 (8.9) | 55.0 (11.9) | 43.7 (6.6) | 10.8 (7.9) | 44.0 |

Example 15

Optimization of Activated Charcoal Levels in Media: Low Levels Give the Best Extrusion and Initiation In this experiment the effects of varying the concentration of activated charcoal were investigated. Media containing a number of different charcoal concentrations were compared. Previous work has shown that activated charcoal adsorbs growth regulators and mineral nutrients, therefore, zinc and copper were increased with increasing activated charcoal concentration, and in the highest charcoal treatment, auxin was increased.

Megagametophyte explants were isolated from the cones of three open-pollinated trees, representing a multiplicity of genotypes. The seeds contained Stage 2–4 zygotic embryos. Seeds were sterilized as described in Example 1. Seed coats were split and the megagametophytes were isolated by removing integuments and nucellus. Isolated megagametophytes were cultured on solid media #504 (Table 47) modified to create six media treatments (Table 39).

The experiment consisted of three replications per treatment, per cone collection. Replications consisted of ten explants in adjacent wells on a single well plate. Plates were wrapped in PARAFILM and incubated in the dark at 23–24° C.

After nine weeks, extrusion and initiation were scored as described in Example 3. Extrusion frequencies were highest in the media containing 50 mg/l activated charcoal (Table 40). Likewise, initiation frequencies were highest using the media containing 50 mg/l activated charcoal (Table 41). These results, as well as the high rates of extrusion and initiation obtained in Examples 13 and 14, demonstrate that low levels of activated charcoal may be used effectively.

TABLE 39

Treatment Media Compositions
Treatment Media Composition-Media #504 plus: (mg/l)

| Treatment | Activated Charcoal (mg/l) | $ZnSO_4 \cdot 7H_3O$ (ppm) | $CuSO_4 \cdot 5H_2O$ (ppm) | Auxin (mg/l) |
|---|---|---|---|---|
| #1 | 0 | 14.40 | 0.125 | 2.0 |
| #2 | 50 | 14.69 | 0.173 | 2.0 |
| #3 | 100 | 14.97 | 0.220 | 2.0 |
| #4 | 250 | 15.84 | 0.363 | 2.0 |
| #5 | 500 | 17.28 | 0.600 | 2.0 |
| #6 | 2500 | 28.80 | 2.5 | 110.0 |

TABLE 40

Extrusion Frequencies
% of Megagametophytes Extruding-Mean (standard error) Genotype

| Treatment | 1033 | 2 | 105 | total |
|---|---|---|---|---|
| #1 (no A.C.) | 16.7 (6.7) | 23.3 (3.3) | 16.7 (6.7) | 18.9 |
| #2 (50 mg/l A.C.) | 26.7 (3.3) | 33.3 (16.7) | 40.0 (0) | 33.3 |
| #3 (100 mg/l A.C.) | 16.7 (3.3) | 23.3 (3.3) | 36.7 (6.7) | 25.6 |
| #4 (250 mg/l A.C.) | 16.7 (6.7) | 20.0 (5.8) | 17.3 (3.7) | 18.0 |
| #5 (500 mg/l A.C.) | 6.7 (3.3) | 16.7 (3.3) | 27.7 (9.1) | 17.0 |
| #6 (2500 mg/l A.C.) | 28.8 (8.8) | 26.7 (3.3) | 17.0 (6.5) | 24.2 |

A.C. - Activated Charcoal

TABLE 41

Initiation Frequencies
% of Megagametophytes Initiating-Mean (standard error) Genotype

| Treatment | 1033 | 2 | 105 | total |
|---|---|---|---|---|
| #1 (no A.C.) | 0 (0) | 0 (0) | 6.7 (0) | 2.2 |
| #2 (50 mg/l A.C.) | 3.3 (3.3) | 10 (5.8) | 3.3 (3.3) | 5.5 |
| #3 (100 mg/l A.C.) | 6.7 (3.3) | 3.3 (3.3) | 3.3 (3.3) | 4.4 |
| #4 (250 mg/l A.C.) | 3.3 (3.3) | 3.3 (3.3) | 0 (0) | 2.2 |

TABLE 41-continued

Initiation Frequencies
% of Megagametophytes Initiating-Mean (standard error) Genotype

| Treatment | 1033 | 2 | 105 | total |
|---|---|---|---|---|
| #5 (500 mg/l A.C.) | 3.3 (3.3) | 0 (0) | 0 (0) | 1.1 |
| #6 (2500 mg/l A.C.) | 0 (0) | 0 (0) | 0 (0) | 0 |

A.C. - Activated Charcoal

Example 16

Optimization of Culture Initiation Using Liquid Media in Loblolly Pine

Several Examples have demonstrated the efficacy of using a liquid initiation media. The results presented in this Example demonstrate the advantage of using small volumes of liquid media when initiating cultures. These results also demonstrate that small early stage embryos can effectively be used as explants in initiating cultures.

The following experiment was repeated on four separate occasions: In each experiment the explant consisted of an excised early zygotic embryo and the megagametophyte from which it was isolated. The embryos were early zygotic embryos at Stage 1, isolated from the summer cones of four different loblolly pine trees, representing four distinct genotypes. Each explant was placed in a single well in a multi-well culture dish. Each experiment consisted of three treatments with a single replication. One set of ten explants was immersed in 0.5 ml of liquid media #1081 (Table 47). A second set of ten explants was immersed in 2.0 ml of media #1081. Simultaneously, a third set of ten explants was cultured on solid media. After eight weeks, the initiation frequency of the explants was evaluated as in Example 3 (Table 42).

The results demonstrate that using 0.5 ml of liquid media is superior to using the larger volume of 2.0 ml. Currently it is unknown why a smaller volume is superior. We speculate that the megagametophyte may produce factors that promote somatic embryogenesis and that these factors are diluted when larger volumes of liquid media are used. Using a small volume of liquid media was also superior to using solid media in initiating cultures.

TABLE 42

Initiation Frequency
% of Megagametophytes Initiating-Mean of four experiments (plus standard error) Genotype

| Treatment | FN | FX | FO | FZ | total |
|---|---|---|---|---|---|
| #1- 0.5 ml liquid | 33.6 (13.0) | 37.4 (12.0) | 16.7 (6.7) | 18.3 (6.9) | 24.1 |
| #2- 2.0 ml liquid | 2.5 (2.5) | 13.3 (6.7) | 6.7 (2.5) | 2.5 (2.5) | 6.3 |
| #3- solid media | 19.1 | 18.9 | 0 | 6.9 | 11.2 |

Example 17

Brassinolide and Elevated Pressure Enhance Embryogenic Culture Initiation in Norway Spruce The previous examples have demonstrated the efficacy of using brassinosteroids and elevated pressure to promote initiation in Loblolly pine. This Example demonstrates that these treatments can effectively promote initiation in Norway spruce.

Explants were zygotic embryos flipped out of the megagametophyte, prepared as in Example 1. The experiment consisted of five replications, with a replication consisting of ten explants in a single petri dish. Explants were cultured on solid media #56 (Table 3). Treatment #1 consisted of explants on media #56. In Treatment #2, the medium additionally contained 1 ppm ABA. In Treatment #3, the media contained 0.1 pM brassinolide. In Treatment #4, the explants were cultured under 1.5 atmospheres of pressure. After ten weeks, the explants were examined and the frequency of embryogenic culture initiation was scored (Table 43).

Initiation frequency was improved in all three treatments relative to the control. ABA, brassinolide and elevated pressure were equally effective in increasing initiation by over 30% of the control frequency. These results, combined with the results of previous Examples, demonstrate that brassinosteroids and elevated pressure are effective in a range of species.

TABLE 43

| Treatment | Initiation Frequency % of Explants Initiating |
|---|---|
| | % Initiating (std. error) |
| #1- control | 34.6 (5.0) |
| #2- ABA added to medium | 47.4 (5.5) |
| #3- Brassinolide added to medium | 46.2 (6.1) |
| #4- Elevated Atmospheric Pressure | 45.0 (4.5) |

Example 18

ABA Pre-treatment Improves Initiation in Norway Spruce

The previous examples have demonstrated a method of pre-treating ovules with ABA in Loblolly pine. This Example demonstrates that such treatments can effectively promote initiation in Norway spruce. In this Example, various ABA pre-treatment methods are compared.

Explants were zygotic embryos flipped out of the megagametophyte, prepared as in Example 1. The experiment consisted of four replications, with a replication consisting of ten explants in a single petri dish. Explants were cultured on solid media lacking ABA. This media was identical to media #56, described in Table 3, however, leachate from the dark filter paper used to visualize the explants eventually reduced the pH to about 4.14.

The treatments were designed to investigate the effects of pre-treating the whole seed compared to treating the explant (i.e. the embryo and megagametophyte) after their removal from the seed. It is presumed that soaking a whole seed will result in less ABA uptake by the megagametophyte and embryo than soaking them directly in ABA due to their being surrounded by seed tissue. Two treatments also compared the effect of the pH of the ABA solution. In Treatment #1, the control, seeds were soaked in water for 24 hours, and then explants were prepared as in Example 1. In Treatment #2, seeds were soaked in 5 ppm ABA for 24 hours prior to explant removal. In Treatment #3, seeds were soaked in 20 ppm ABA for 24 hours prior to explant removal. In Treatment #4, seeds were soaked in water for 24 hours and then the explants were removed and soaked in a 5 ppm ABA solution of pH 4.5 for 30 minutes. In Treatment #5 seeds were soaked in water for 24 hours and then the explants were removed and soaked in a 5 ppm ABA solution of pH 5.5 for 30 minutes. After ten weeks, the explants were examined and the frequency of embryogenic culture initiation was scored (Table 44).

Initiation frequency was improved in all treatments relative to the control, demonstrating that pre-treatment with ABA can promote initiation on a media that is free of ABA. Pre-treatment of the seed with a higher concentration of ABA (Treatment #3) or directly soaking the explant in ABA (Treatments #4 and #5) were more effective than treating the whole seed at 5 ppm (Treatment #2). One would expect higher ABA uptake by seeds soaked in a higher concentration of ABA. Also, one would expect higher ABA uptake when the embryo is soaked directly, as opposed to being exposed to the ABA solution in the seed. These results suggest that, within the ranges of this experiment, a higher ABA uptake promotes greater initiation. The greater initiation in Treatment #5 than #4 suggests that ABA uptake is higher at pH 4.5 than 5.5.

TABLE 44

| Treatment | Initiation Frequency % of Explants Initiating |
|---|---|
| | % Initiating (std. error) |
| #1- (control) seed soaked in water | 2.5 (2.5) |
| #2- seed soaked in 5 ppm ABA | 15.1 (6.6) |
| #3- seed soaked in 20 ppm ABA | 24.0 (5.4) |
| #4- explant soaked in 5 ppm ABA (pH 5.5) | 22.0 (3.0) |
| #5- explant soaked in 5 ppm ABA (pH 4.5) | 31.2 (12.2) |

Example 19

Brassinolide, ABA Pre-treatment and Elevated Atmospheric Pressure Improve Initiation in Douglas Fir Previous Examples have demonstrated that brassinolide, ABA and elevated atmospheric pressure increase initiation in Loblolly pine. This Example demonstrates that such treatments can effectively promote initiation in Douglas fir.

The explants used in this experiment were isolated from Douglas fir cones collected in mid-summer from four open-pollinated trees, representing a multiplicity of genotypes. Explants were stage 3–5 (early-midstage) zygotic embryos attached to megagametophytes, prepared as described in Example 2. The embryo and attached megagametophyte were then placed next to each other on the treatment media. As in Example 2, each replication consisted of ten explants in a single petri dish. Each treatment contained four replications per treatment, per genotype.

The treatment media were based on solid media #121, the composition of which is described in Table 5. Media #121 contains no ABA or brassinolide. Treatment #1, the control, consisted of explants cultured on media #121 alone. In Treatment #2, explants were cultured on media #121 containing 0.1 $\mu$M brassinolide. In Treatment #3, explants were cultured on media #121 containing 1 ppm ABA. In treatment #4, explants were soaked in liquid media containing 5 ppm ABA for 30 minutes prior to being placed on #121 media. In Treatment #5, explants were cultured on media #121 under 1.5 atmospheres of pressure. The petri dishes were wrapped in PARAFILM and incubated at 23–24° C. in the dark.

Initiation frequency is summarized in Table 45. All treatments increased initiation over that in the control treatment. Explants soaked in an ABA solution prior to culturing had higher initiation frequency than those cultured on media containing ABA, suggesting that pre-culture soaking is a more effective means of delivering ABA to the explant than direct media contact. As in Loblolly pine, elevated atmospheric pressure and brassinolide treatments both substantially increased initiation. The fact that these treatments are effective in Loblolly pine, Norway spruce and Douglas fir demonstrates that these methods may be applied to a broad range of taxonomically divergent conifers.

TABLE 45

Douglas fir explant embryogenic culture initiation frequencies.
% of Megagametophytes Initiating -Mean
Genotype

| Treatment | T02321 | T05251 | T02931 | T02351 | total |
|---|---|---|---|---|---|
| #1 (Media #121) | 10.5 | 0 | 29.6 | 26.3 | 16.6 |
| #2 (+0.1 μM Br) | 27.8 | 30.0 | 34.6 | 21.8 | 31.1 |
| #3 (+1 ppm ABA) | 21.1 | 10.0 | 34.6 | 10.5 | 19.1 |
| #4 (ABA pre-soak) | 27.6 | 20.0 | 26.9 | 25.0 | 24.6 |
| #5 (1.5 Atm pressure) | 19.2 | 44.4 | 41.7 | 40.0 | 36.3 |

Example 20

Brassinolide and Elevated Atmospheric Pressure Improve the Growth of Embryogenic Cultures in Rice This example demonstrates the broad applicability of certain aspects of the invention to taxonomically diverse species. In this experiment, brassinolide and elevated atmospheric pressure improved the initiation of embryogenic cultures in rice (*Oryza sativa*). Rice, an annual angiosperm, is quite taxonomically distant from the conifers used in previous examples. However, as this example makes clear, brassinosteroids and elevated atmospheric pressure effectively increase embryogenic culture initiation of in a wide variety of species.

In this experiment, four initiation treatments were studied, using explants from mature Japaonica rice seeds (cultivar Taipei 309). The explants were dehulled sterilized seeds. About 400 mature seeds were dehulled and surface sterilized in a 5.25% bleach solution for 25 minutes and then rinsed three times with sterile deionized water. About 70 explants were placed into each of four treatment petri dishes containing solid media. The explants were placed with the embryo side up. The basal media was a Murashige and Skoog (MS) media containing 2.0 mg/l 2,4-D. Plates were wrapped in PARAFILM and cultured in the dark at 27° for two weeks.

Treatment 1, the control treatment, consisted of the above-described basal media, contained no brassinolide, and was cultured at atmospheric pressure. Treatment 2 contained the basal media and was cultured at 1.5 atm of pressure. Treatment 3 contained basal to which 0.1 μM brassinolide was added and was cultured at normal atmospheric pressure. Treatment 4 contained basal media to which 1 μM brassinolide was added and was cultured at atmospheric pressure.

After two weeks, embryogenic callus had developed on most of the explants. The embryogenic callus formed in spherical formations around the embryo. During culture, the scutellum elongated and the embryogenic calli formed masses around the base of the scutellum, covering and obscuring the rest of the embryo. Initiation was scored by measuring the diameter of the embryogenic callus on each explant. A larger callus contains more somatic embryos and thus has a greater potential to supply viable embryos for subsequent regeneration of whole plants. Callus size was measured by observing callus under a dissecting scope fitted with an ocular measurement device allowing accurate measurements to 0.1 mm.

Average callus size in each treatment is summarized in Table 46. Culturing at 1.5 atmospheres of pressure significantly increased average callus size over that in the control treatment (LSD test at p<0.95). Likewise, average callus size was significantly increased by the addition of 0.1 μM brassinolide to the media. The addition of 1.0 μM brassinolide did not increase callus size, indicating that this concentration of brassinosteroid is above optimal.

These results demonstrate that both brassinosteroids and elevated atmospheric pressure can effectively improve the initiation of embryogenic culture in rice, as they do in conifers. The successful use of brassinosteroids and pressure in such taxonomically divergent species supports the broad applicability of these factors to initiation of any plant species.

TABLE 46

Initiation Vigor in Rice
Callus Diameter

| Treatment | Diameter (mm) + (std. error) |
|---|---|
| #1- (control) | 4.28 (0.12) |
| #2- 1.5 atmospheres pressure | 4.71 (0.10) |
| #3- +0.1 μM Brassinolide | 4.70 (0.13) |
| #4- +1.0 μM Brassinolide | 4.19 (0.12) |

Example 21

Improving Embryogenic Culture Initiation in Soybean Using Brassinosteroids and Elevated Atmospheric Pressure The efficiency of somatic embryogenesis in dicotyledenous species can be improved by adding brassinosteroids to the initiation medium, or culturing under elevated atmospheric pressure. Both methods can be simultaneously applied to further increase the initiation of embryogenic cultures of soybean.

In one example, immature zygotic embryos from soybean (*Glycine max*) can provide explants for embryogenic culture initiation. Cotyledons are excised from the seeds. The end of the cotyledon containing the embryogenic axis are removed and then placed on solid initiation media with the flat side of the explant facing upwards. The explants can be cultured in low light (5–10 μE $m^{-2}$ $s^{-1}$) or the dark for up to six weeks.

The initiation medium can be any medium known in the art to be effective for soybean culture. In one embodiment, the media is solid MS medium, additionally containing B5 vitamins, 3% sucrose, 40 mg/l 2,4-D and 0.2% gellan gum at a pH of 7.0. The media may contain 0.01 to 0.25 μM or more brassinosteroids to increase the efficiency of embryogenic culture initiation. For example, brassinolide at 0.1 μM concentration may be added to the media to promote embryogenic culture initiation. The explants or whole seeds can also be cultured at elevated atmospheric pressure to increase the efficiency of embryogenic culture initiation. In one embodiment, explants are cultured at 1.5 atmospheres of pressure.

TABLE 47

Media Compositions

| Components | mg/l | | | | | | | |
|---|---|---|---|---|---|---|---|---|
| | #504 | #716 | #887 | #888 | #889 | #897 | #945 | #971 |
| $NH_4NO_3$ | 200.0 | 200.0 | 200.0 | 200.0 | 200.0 | 200.0 | 200.0 | 200.0 |
| $KNO_3$ | 909.9 | 909.9 | 909.9 | 909.9 | 909.9 | 909.9 | 909.9 | 909.9 |
| $KH_2PO_4$ | 136.1 | 136.1 | 136.1 | 136.1 | 136.1 | 136.1 | 136.1 | 136.1 |
| $Ca(NO_3)_2.4H_2O$ | 236.2 | 236.2 | 236.2 | 236.2 | 236.2 | 236.2 | 236.2 | 236.2 |
| $MgSO_4.7H_2O$ | 246.5 | 246.5 | 246.5 | 246.5 | 246.5 | 246.5 | 246.5 | 246.5 |
| $Mg(NO_3)_2.6H_2O$ | 256.5 | 256.5 | 256.5 | 256.5 | 256.5 | 256.5 | 256.5 | 256.5 |
| $MgCl_2.6H_2O$ | 101.7 | 101.7 | 101.7 | 101.7 | 101.7 | 101.7 | 101.7 | 101.7 |
| KI | 4.15 | 4.15 | 4.15 | 4.15 | 4.15 | 4.15 | 4.15 | 4.15 |
| $H_3BO_3$ | 15.5 | 15.5 | 15.5 | 15.5 | 15.5 | 15.5 | 15.5 | 15.5 |
| $MnSO_4.H_2O$ | 10.5 | 10.5 | 10.5 | 10.5 | 10.5 | 10.5 | 10.5 | 10.5 |
| $ZnSO_4.7H_3O$ | — | 14.67 | 14.67 | 14.67 | 14.67 | 14.67 | 14.67 | 14.67 |
| $Na_2MoO_4.2H_2O$ | 0.125 | 0.125 | 0.125 | 0.125 | 0.125 | 0.125 | 0.125 | 0.125 |
| $CuSO_4.5H_2O$ | — | 0.1725 | 0.1725 | 0.1725 | 0.1725 | 0.1725 | 0.1725 | 0.1725 |
| $CoCl_2.6H_2O$ | 0.125 | 0.125 | 0.125 | 0.125 | 0.125 | 0.125 | 0.125 | 0.125 |
| $FeSO_4.7H_2O$ | 13.9 | 13.9 | 13.9 | 13.9 | 13.9 | 13.9 | 13.9 | 13.9 |
| $Na_2EDTA$ | 18.65 | 18.65 | 18.65 | 18.65 | 18.65 | 18.65 | 18.65 | 18.65 |
| Maltose | 15,000 | 15,000 | 15,000 | 15,000 | 15,000 | 15,000 | 15,000 | 15,000 |
| myo-Inositol | 20,000 | 20,000 | 20,000 | 20,000 | 20,000 | 20,000 | 20,000 | 20,000 |
| Casamino Acids | 500 | 500 | 500 | 500 | 500 | 500 | 500 | 500 |
| L-Glutamine | 450 | 450 | 450 | 450 | 450 | 450 | 450 | 450 |
| Thiamine.HCl | 1.0 | 1.0 | 1.0 | 1.0 | 1.0 | 1.0 | 1.0 | 1.0 |
| Pyridoxine.HCL | 0.5 | 0.5 | 0.5 | 0.5 | 0.5 | 0.5 | 0.5 | 0.5 |
| Nicotinic acid | 0.5 | 0.5 | 0.5 | 0.5 | 0.5 | 0.5 | 0.5 | 0.5 |
| Glycine | 2.0 | 2.0 | 2.0 | 2.0 | 2.0 | 2.0 | 2.0 | 2.0 |
| NAA | — | 2.0 | 2.0 | 2.0 | 2.0 | — | 2.0 | 2.0 |
| BAP | 0.45 | 0.45 | 0.55 | 0.55 | 0.55 | — | 0.63 | 0.55 |
| Kinetin | 0.43 | 0.43 | 0.53 | 0.53 | 0.53 | — | 0.61 | 0.53 |
| CGMP* | — | — | — | — | 10 μM | — | 10 μM | — |
| $AgNO_3$ | — | 3.398 | — | 3.398 | 3.398 | — | 3.398 | — |
| Activated Charcoal | — | 50 | 50 | 50 | 50 | 50 | 50 | — |
| ABA* | — | 1.0 | 1.0 | 1.0 | 1.0 | — | 1.0 | — |
| Brassinolide* | — | — | — | — | — | — | — | — |
| GELRITE | 2,000 | 2,000 | 2,000 | 2,000 | 2,000 | 2,000 | 2,000 | 2,000 |
| pH | 5.7 | 5.7 | 5.7 | 5.7 | 5.7 | 5.7 | 5.7 | 5.7 |

| Media Components | mg/l | | | | | | |
|---|---|---|---|---|---|---|---|
| | #972 | #1036 | #1038 | #1042 | #1043 | #1071 | #1081 |
| $NH_4NO_3$ | 200.0 | 200.0 | 200.0 | 200.0 | 200.0 | 200.0 | 200.0 |
| $KNO_3$ | 909.9 | 909.9 | 909.9 | 909.9 | 909.9 | 909.9 | 909.9 |
| $KH_2PO_4$ | 136.1 | 136.1 | 136.1 | 136.1 | 136.1 | 136.1 | 136.1 |
| $Ca(NO_3)_2.4H_2O$ | 236.2 | 236.2 | 236.2 | 236.2 | 236.2 | 236.2 | 236.2 |
| $MgSO_4.7H_2O$ | 246.5 | 246.5 | 246.5 | 246.5 | 246.5 | 246.5 | 246.5 |
| $Mg(NO_3)_2.6H_2O$ | 256.5 | 256.5 | 256.5 | 256.5 | 256.5 | 256.5 | 256.5 |
| $MgCl_2.6H_2O$ | 101.7 | 101.7 | 101.7 | 101.7 | 101.7 | 101.7 | 101.7 |
| KI | 4.15 | 4.15 | 4.15 | 4.15 | 4.15 | 4.15 | 4.15 |
| $H_3BO_3$ | 15.5 | 15.5 | 15.5 | 15.5 | 15.5 | 15.5 | 15.5 |
| $MnSO_4.H_2O$ | 10.5 | 10.5 | 10.5 | 10.5 | 10.5 | 10.5 | 10.5 |
| $ZnSO_4.7H_3O$ | — | 14.67 | 14.67 | 14.67 | 14.67 | 14.67 | 14.67 |
| $Na_2MoO_4.2H_2O$ | 0.125 | 0.125 | 0.125 | 0.125 | 0.125 | 0.125 | 0.125 |
| $CuSO_4.5H_2O$ | — | 0.1725 | 0.1725 | 0.1725 | 0.1725 | 0.1725 | 0.1725 |
| $CoCl_2.6H_2O$ | 0.125 | 0.125 | 0.125 | 0.125 | 0.125 | 0.125 | 0.125 |
| $FeSO_4.7H_2O$ | 13.9 | 13.9 | 13.9 | 13.9 | 13.9 | 13.9 | 13.9 |
| $Na_2EDTA$ | 18.65 | 18.65 | 18.65 | 18.65 | 18.65 | 18.65 | 18.65 |
| Maltose | 15,000 | 15,000 | 15,000 | 15,000 | 15,000 | 15,000 | 15,000 |
| myo-Inositol | 20,000 | 20,000 | 20,000 | 20,000 | 20,000 | 20,000 | 20,000 |
| Casamino Acids | 500 | 500 | 500 | 500 | 500 | 500 | 500 |
| L-Glutamine | 450 | 450 | 450 | 450 | 450 | 450 | 450 |
| Thiamine.HCl | 1.0 | 1.0 | 1.0 | 1.0 | 1.0 | 1.0 | 1.0 |
| Pyridoxine.HCL | 0.5 | 0.5 | 0.5 | 0.5 | 0.5 | 0.5 | 0.5 |
| Nicotinic acid | 0.5 | 0.5 | 0.5 | 0.5 | 0.5 | 0.5 | 0.5 |
| Glycine | 2.0 | 2.0 | 2.0 | 2.0 | 2.0 | 2.0 | 2.0 |
| NAA | 2.0 | 2.0 | 0.5 | 2.0 | 2.0 | 0.3 | 0.3 |
| BAP | 0.55 | 0.63 | 0.63 | 0.63 | 0.63 | 0.63 | 0.63 |
| Kinetin | 0.53 | 0.61 | 0.61 | 0.61 | 0.61 | 0.61 | 0.61 |
| cGMP* | — | 10 μM | 10 μM | 10 μM | 10 μM | 10 μM | 10 μM |
| $AgNO_3$ | 3.398 | 3.398 | 3.398 | 3.398 | 3.398 | 3.398 | 3.398 |

TABLE 47-continued

Media Compositions

| Activated Charcoal | 50 | 50 | 50 | 50 | 50 | 50 | 50 |
|---|---|---|---|---|---|---|---|
| ABA* | 1.0 | 1.0 | 1.0 | — | — | 1.0 | 1.0 |
| Brassinolide* | — | — | — | — | 0.1 µM | — | 0.1 µM |
| GELRITE | 2,000 | — | — | 2,000 | 2,000 | — | — |
| pH | 5.7 | 5.7 | 5.7 | 5.7 | 5.7 | 5.7 | 5.7 |

The specification is most thoroughly understood in light of the teachings of the references cited within the specification, all of which are hereby incorporated by reference in their entirety. The embodiments within the specification provide an illustration of embodiments of the invention and should not be construed to limit the scope of the invention. The skilled artisan recognizes that many other embodiments are encompassed by the claimed invention and that it is intended that the specification and examples be considered as exemplary only, with a true scope and spirit of the invention being indicated by the following claims.

We claim:

1. A method of initiating coniferous plant somatic embryogenic cultures comprising placing a suitable explant in a liquid initiation medium containing effective amounts of auxin, cytokinin, and nutrients, under suitable environmental conditions such that a culture is formed containing at least one somatic embryo.

2. The method of claim 1 wherein the liquid initiation medium comprises about 0 to 2.5 g/l agar, 0 to 0.5 g/l gellan gum, or 0 to 3.0 g/l agarose.

3. The method of claim 1 wherein the liquid initiation medium contains no gelling agent.

4. The method of claim 1 wherein the liquid initiation medium is substantially free of abscisic acid.

5. The method of claim 1 wherein the liquid initiation medium contains an effective amount of abscisic acid.

6. The method of claim 1 wherein an effective amount of auxin is from 0 to 5.0 mg/l and wherein an effective amount of cytokinin is from 0 to 1.5 mg/l.

7. The method of claim 1 wherein the liquid medium contains an effective concentration of a brassinosteroid.

8. The method of claim 7 wherein an effective concentration of brassinosteroid is 0.05 to about 0.25 µM.

9. The method of claim 7 wherein the explant is exposed to 1.1 to 5.0 atmospheres of pressure.

10. The method of claim 1 wherein the liquid medium contains an effective concentration of a brassinosteroid and the cultured explant is exposed to 1.1 to 5.0 atmospheres of pressure.

11. The method of claim 1 wherein
 (a) the liquid initiation medium contains:
  0.1 to 120 mg/l auxin;
  0.1 to 100 mg/l cytokinin;
  1 to 70 g/l of a readily metabolized carbohydrate;
  0 to 2500 mg/l activated charcoal;
  0 to 10 mg/l silver nitrate;
  0.01 to 0.25 µM of a brassinosteroid;
  1 to 100 mg/l abscisic acid; and
 (b) the cultured explant is exposed to 1.1 to 5.0 atmospheres of pressure.

12. The method of claim 1 wherein
 (a) the liquid initiation medium contains:
  0.1 to 5.0 mg/l auxin;
  0.1 to 1.5 mg/l cytokinin;
  1 to 70 g/l of a readily metabolized carbohydrate;
  0 to 50 mg/l activated charcoal;
  0 to 10 mg/l silver nitrate;
  0.01 to 0.25 µM of a brassinosteroid;
  1 to 100 mg/l abscisic acid; and
 (b) the cultured explant is exposed to 1.1 to 5.0 atmospheres of pressure.

13. A method of initiating coniferous plant somatic embryogenic cultures comprising:
 (a) pretreating a suitable explant in a solution containing an effective amount of abscisic acid; and
 (b) culturing the explant using a medium containing effective amounts of auxin, cytokinin and nutrients, under suitable environmental conditions such that a culture is formed containing at least one somatic embryo.

14. The method of claim 13 wherein the medium is a liquid media.

15. The method of claim 13 wherein the medium is a solid medium substantially free of abscisic acid.

16. The method of claim 13 wherein the pretreated explant is washed with a solution free of abscisic acid prior to placing the explant into liquid culture.

17. A method of initiating coniferous plant somatic embryogenic cultures comprising:
 (a) placing pre-extrusion megagametophytes that contain immature zygotic embryos on a solid culture medium substantially free of abscisic acid and containing a sufficient amount of nutrients and hormones under suitable environmental conditions such that embryogenic tissue is extruded from the megagametophytes; and
 (b) culturing at least one mass of extruded tissue in liquid initiation medium containing a sufficient amount of nutrients and hormones under suitable environmental conditions such that the extruded tissue proliferates into a culture containing at least one somatic embryo.

18. The method of claim 17 wherein the liquid initiation medium comprises about 0 to 2.5 g/l agar, 0 to 0.5 g/l gellan gum, or 0 to 3.0 g/l agarose.

19. The method of claim 17 wherein the liquid initiation medium contains no gelling agent.

20. The method of claim 17 wherein the extruded tissue is transferred to liquid culture initiation medium.

21. The method of claim 17 wherein the solid medium is contained within a vessel and sufficient liquid initiation medium is added to the vessel to submerge the embryogenic tissue.

22. The method of claim 17 wherein the liquid initiation medium contains 0.1 to 100 mg/l abscisic acid.

23. The method of claim 17 wherein:
 (a) the solid medium contains:
  0.1 to 120 mg/l auxin;
  0.1 to 100 mg/l cytokinin;
  1 to 70 g/l of a readily metabolized carbohydrate;
  0 to 2500 mg/l activated charcoal;
  0 to 10 mg/l silver nitrate;
  0.01 to 0.25 µM of a brassinosteroid;

(b) the megagametophyte is exposed to 1.1 to 5.0 atmospheres of pressure prior to culture in the liquid medium;
(c) the liquid initiation medium contains:
0.1 to 120 mg/l auxin;
0.1 to 100 mg/l cytokinin;
0 to 70 g/l of a readily metabolized carbohydrate;
0 to 2500 mg/l activated charcoal;
0 to 10 mg/l silver nitrate;
0.01 to 0.25 µM of a brassinosteroid;
1 to 100 mg/l abscisic acid; and
(d) the megagametophyte is exposed to 1.1 to 5.0 atmospheres of pressure while in the liquid medium.

24. The method of claim 17 wherein:
(a) the solid medium contains:
0.1 to 5.0 mg/l auxin;
0.1 to 1.5 mg/l cytokinin;
1 to 70 g/l of a readily metabolized carbohydrate;
0 to 50 mg/l activated charcoal;
0 to 10 mg/l silver nitrate;
0.01 to 0.25 µM of a brassinosteroid;
(b) the megagametophyte is exposed to 1.1 to 5.0 atmospheres of pressure prior to culture in the liquid medium;
(c) the liquid initiation medium contains:
0.1 to 5.0 mg/l auxin;
0.1 to 1.5 mg/l cytokinin;
0 to 70 g/l of a readily metabolized carbohydrate;
0 to 50 mg/l activated charcoal;
0 to 10 mg/l silver nitrate;
0.01 to 0.25 µM of a brassinosteroid;
1 to 100 mg/l abscisic acid; and
(d) the megagametophyte is exposed to 1.1 to 5.0 atmospheres of pressure while in the liquid medium.

25. A medium for promoting the initiation of somatic embyrogenesis in plants comprising an effective amount of auxin, cytokinin and nutrients and, further comprising an effective amount of a brassinosteroid.

26. The medium of claim 25 wherein the brassinosteroid is selected from the group consisting of brassinolide and brassinolide analogs.

27. The medium of claim 25 wherein an effective concentration of brassinosteroid comprises 0.005 µM to about 0.25 µM.

28. A method of initiating somatic embryogenesis in plants comprising culturing suitable explants using the medium of claim 25 until somatic embryogenesis is initiated.

29. A method of initiating somatic embryogenesis in plants by exposing cultured tissues to 1.1 to 5.0 atmospheres of pressure until somatic embryogenesis is initiated.

30. The method of claim 29 wherein the tissues are cultured at 1.5 to 5.0 atmospheres of pressure.

31. The method of claim 29 wherein the tissues are cultured at about 1.5 atmospheres of pressure.

32. A method of promoting extrusion of embryogenic tissue in cultured megagametophytes by exposing cultured tissues to 1.1 to 5.0 atmospheres of pressure until extrusion is evident.

33. The method of claim 32 wherein the tissues are cultured at 1.5 to 5.0 atmospheres of pressure.

34. The method of claim 32 wherein the tissues are cultured at about 1.5 atmospheres of pressure.

35. A method of promoting initiation of embryogenic cultures in Gymnosperms or Angiosperms comprising exposing cultured tissues to at least 0.1 atm above ambient atmospheric pressure until initiation is evident.

36. A method of promoting initiation of embryogenic cultures in Gymnosperms and Angiosperms by exposing cultured tissues to 1.1 to 5.0 atmospheres of pressure until initiation is evident.

37. The method of claim 36 wherein the tissues are cultured at 1.5 to 5.0 atmospheres of pressure.

38. The method of claim 36 wherein the tissues are cultured at about 1.5 atmospheres of pressure.

39. A method of promoting the initiation of somatic embryogenesis in plants comprising:
(a) culturing suitable explants using a medium comprising an effective amount of a brassinosteroid and effective amounts of auxin, cytokinin and nutrients; and
(b) exposing cultured tissues to 1.1 to 5.0 atmospheres of pressure until initiation is evident.

40. The method of claim 1 wherein the liquid medium contains less than 500 mg/l activated charcoal.

41. The method of claim 17 wherein the liquid medium contains less than 500 mg/l activated charcoal.

42. The method of claim 40 wherein the liquid medium contains less than 50 mg/l activated charcoal.

43. The method of claim 41 wherein the liquid medium contains less than 50 mg/l activated charcoal.

* * * * *

UNITED STATES PATENT AND TRADEMARK OFFICE
CERTIFICATE OF CORRECTION

PATENT NO.  : 6,492,174 B1 Page 1 of 1
DATED       : December 10, 2002
INVENTOR(S) : Gerald S. Pullman and Gary Peter It is certified that error appears in the above-identified patent and that said Letters Patent is hereby corrected as shown below:

<u>Column 52,</u>
Line 27, "media" should read -- medium --.

Signed and Sealed this

Fourth Day of March, 2003

JAMES E. ROGAN
*Director of the United States Patent and Trademark Office*